(12) United States Patent
Elashvili

(10) Patent No.: US 6,897,032 B1
(45) Date of Patent: May 24, 2005

(54) METHOD FOR DETECTING G- AND V-AGENTS OF CHEMICAL WARFARE AND THEIR DEGRADATION PRODUCTS

(75) Inventor: Ilya Elashvili, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 548 days.

(21) Appl. No.: 10/131,996

(22) Filed: Apr. 23, 2002

(51) Int. Cl.⁷ ................................................ C12N 9/14
(52) U.S. Cl. ........................................ 435/18; 435/195
(58) Field of Search .................................... 435/18, 195

Primary Examiner—Jean C. Witz
(74) Attorney, Agent, or Firm—Ulysses John Biffoni

(57) ABSTRACT

Methods are described for detecting chemical warfare agents that contain organophosphorus compounds. Compositions containing either (1) a sufficient amount of phosphonate ester hydrolase with an alkali agent or (2) a sufficient amount of phosphonate ester hydrolase, a sufficient amount of organophosphorus hydrolase and a sufficient amount of a organophosphorus acid anhydrolase, may be utilized to test for organophosphorus compound-containing chemical warfare agents. These enzymes will react with such chemical warfare agents to produce degradation products, specifically phosphonate esters.

27 Claims, 35 Drawing Sheets

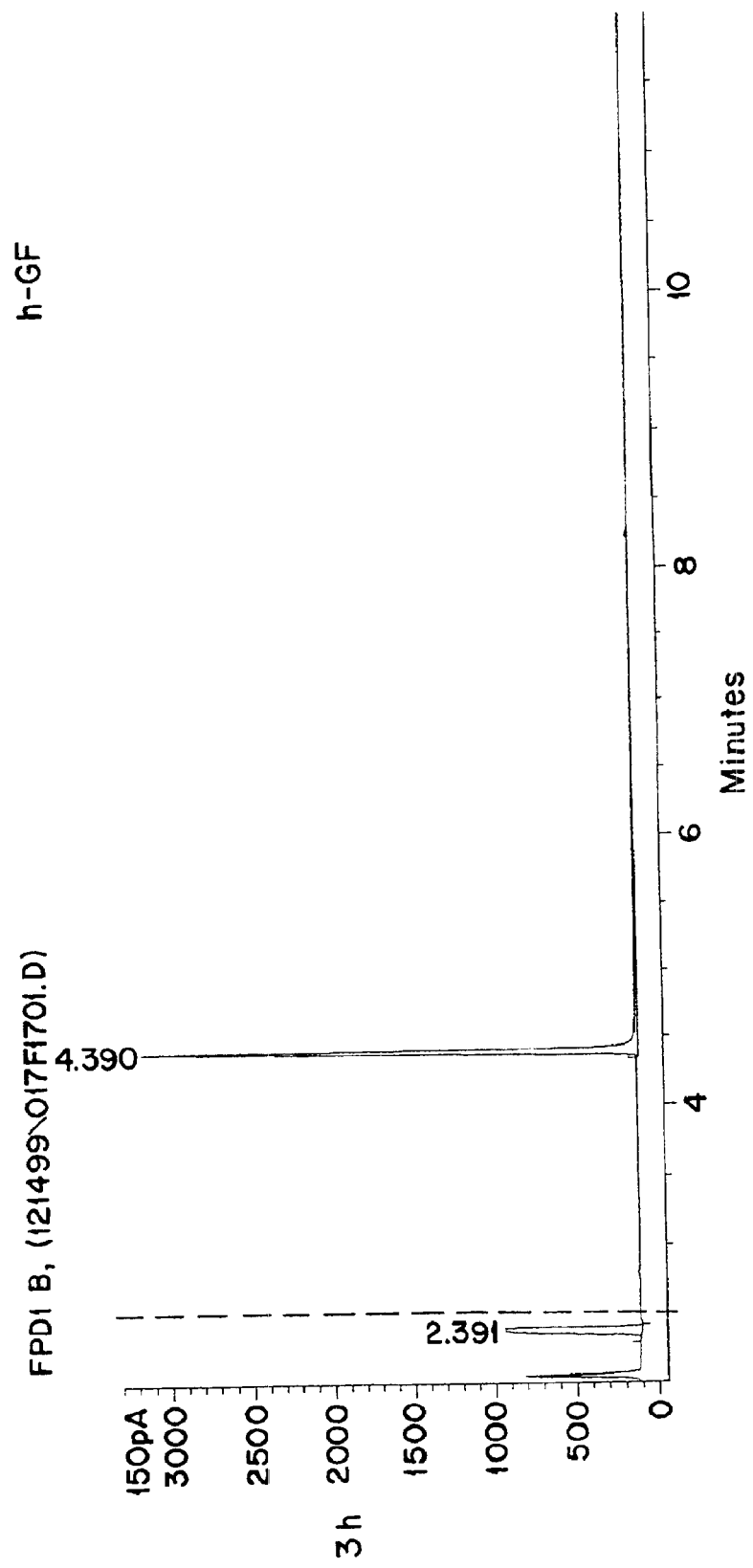

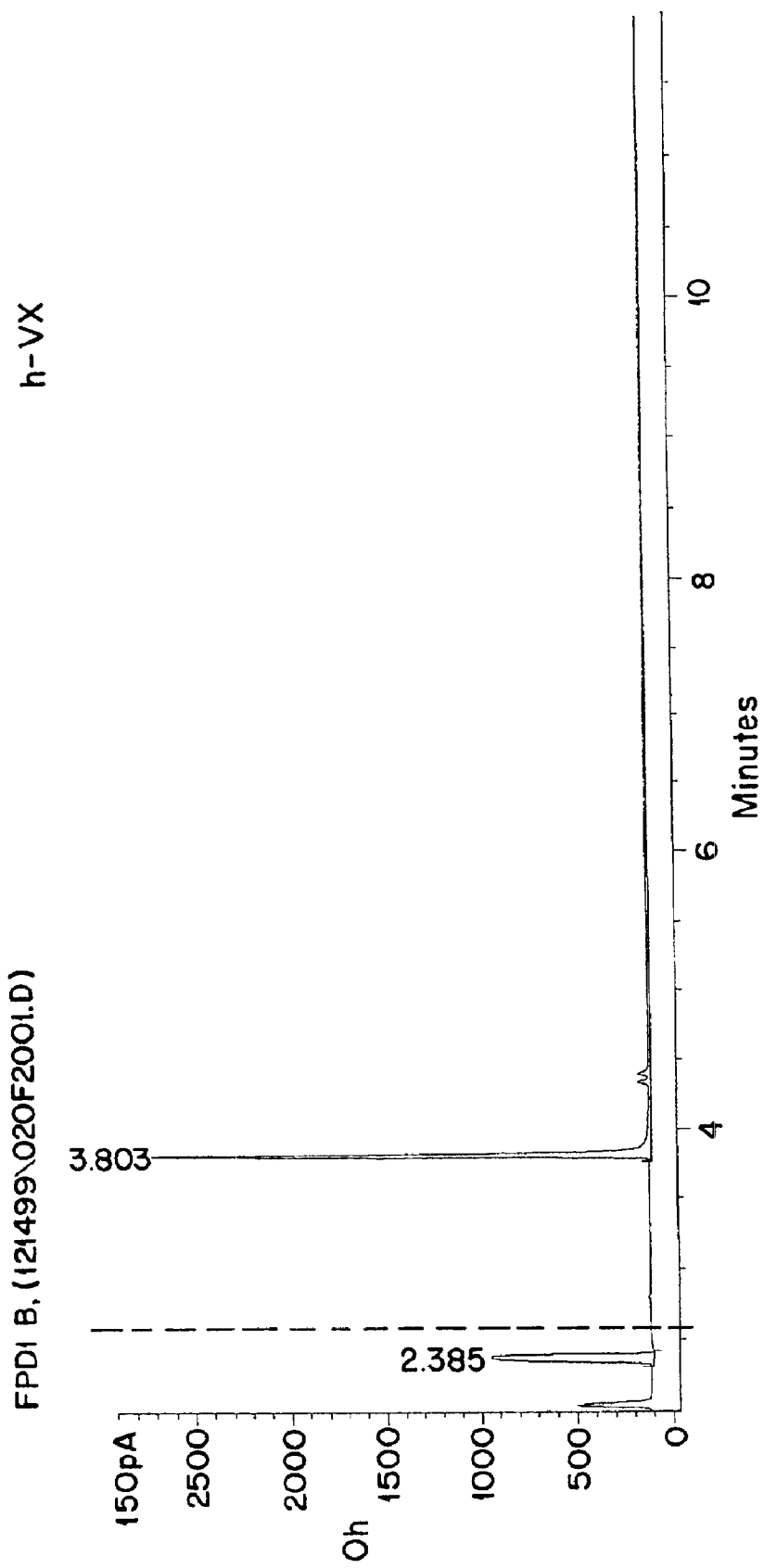

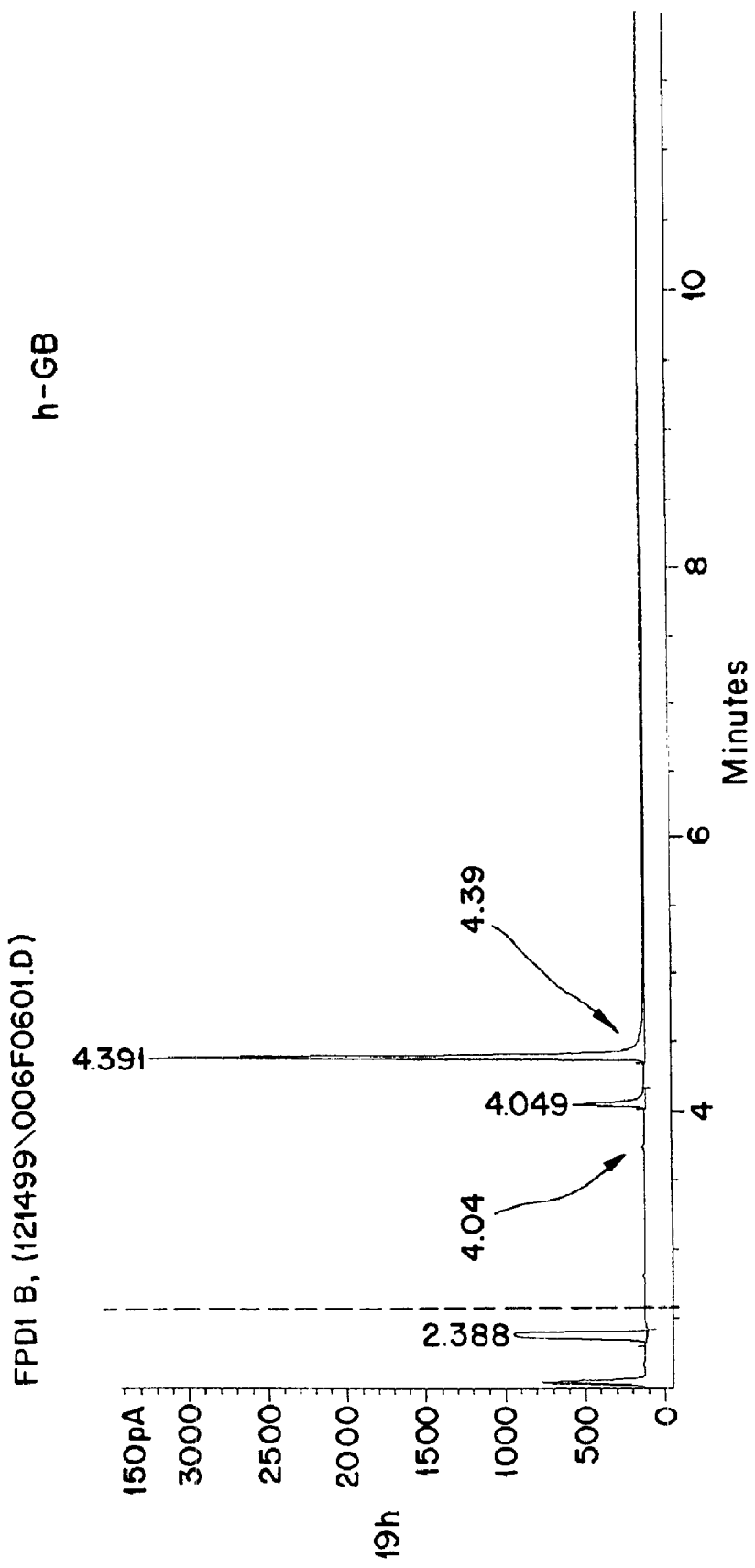

FIG. 7A h-R-VX

FPD1 B, (040500\005F0501.D)

FPD1 B, (040500\013F3201.D)

1 h

Peaks: 3.459, 4.181, 4.655

X-axis: Minutes (0 to 16)
Y-axis: Counts (200000 to 1000000)

FIG. 7F

METHOD FOR DETECTING G- AND V-AGENTS OF CHEMICAL WARFARE AND THEIR DEGRADATION PRODUCTS

CROSS-REFERENCE TO RELATED APPLICATIONS

This patent application is related to patent application Ser. No. 10/131,946 which is hereby incorporated by reference herein.

GOVERNMENT INTEREST

The invention described herein may be manufactured, used and licensed by or for the U.S. Government.

FIELD OF THE INVENTION

This invention relates to methods and kits for detecting the presence of chemical warfare agents and degradation products thereof. More particularly, the invention relates to an accurate and rapid method of detecting in a sample the presence of chemical warfare agents containing organophosphorus compounds.

BACKGROUND OF THE INVENTION

Current methodologies for the detection and analysis of G- and V-type chemical warfare agents (CWA) containing phosphonate esters and their products are inadequate. G-type CWA's include GB, GD and GF, and V-type CWA's include VX and Russian VX. Examples of typical neurotoxic chemical warfare agents are depicted by the following formula I:

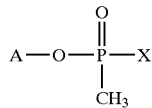

where A is an alkyl group in both G- and V-type compounds, X is fluorine in GB, GD and GF, and X is a mercaptan group in V-type agents. The existing techniques for identification of chemical warfare organophosphorus compounds (OP) rely on multi-faceted analytical data integration, and are further complicated because of the lack of adequate generic analytical methods for these compounds. They fail to rapidly detect and identify known G- and V-agents, not to mention the detection and analysis of unknown agents. The information gathered from them is inferential, time consuming, non-generic, needs expensive and extensive instrumentation, and is ineffective for the analysis and identification of unknown agents. Even known agents require confirmatory multi-instrumental analysis for reliable identification. This involves larger sample quantities and extensive effort. Further, G- and V-type agents differ in their stability characteristics, but in aqueous environments, undergo a slow spontaneous hydrolysis producing very stable methylphosphonate esters as the major phospho-products. These esters were reportedly the major metabolites after GB exposure in humans (see reference 12, listed below) and GB, GD, and GF exposure in rats (see reference 13). Because of the labile nature of these chemical warfare neurotoxins, rapid detection and analysis methodology is also needed for phosphonate ester degradation products, which are important biomarkers.

One current method, the cholinesterase inhibition assay (ChE), could indicate the presence of a chemical warfare agent containing organophosphorus compounds. However, the ChE assays are non-specific (detecting both OP and carbamates) and are subject to interferences from heavy metals. Therefore, these assays cannot even provide the information as to whether the inhibition was due to carbamates or OP, not to mention the capability to ascertain the presence of CW OP neurotoxins.

The most important nerve agents to which the process of this invention can be applied are those containing organophosphorus compounds such as, for instance isopropyl methylphosphonofluoridate (GB), pinacolyl methylphosphonofluoridate (GD), cyclohexyl methylphosphonofluoridate (GF), O-ethyl S-(2-diisopropylamino)ethyl methylphosphonothiolate (VX), and O-isobutyl S-(2-diethyl-aminoethyl) methylphosphonothioate (Russian VX or R-VX). Note that the designations GB, GD, GF, VX, and Russian VX refer to standard U.S. government designations for the respective chemical warfare agents.

As employed herein, the term "chemical warfare agent," which is sometimes abbreviated as "CWA", is intended to include only those agents which are effective in relatively small dosages to substantially disable or kill mammals. The term "chemical warfare agent" in this application includes substantially pure chemical compounds, but the term also contemplates mixtures of the aforesaid agents in any proportions, as well as those agents in impure states in which the other components in the mixture are not simply other CWA's. "Chemical warfare agents," as used herein, also includes partially or completely degraded CWA's, e.g., the gelled, polymerized, or otherwise partially or totally decomposed chemical warfare agents commonly found to be present in old munitions.

In view of the advantages of rapidly and accurately identifying the presence of CW OP agents and associated by-products, and further in view of the need to address the shortcomings associated with currently available detection methods, there is still a need for new and improved detection methods and kits. The present invention addresses these needs.

BRIEF DESCRIPTION OF THE FIGURES

FIG. 3 shows PEH degradation of h-GF and h-GD. The timeline of the GC-FPD chromatograms of the PEH reactions at 30° C. with the two (h-GF and h-GD) out of the total of five substrates (ca. 10 mM) and their controls are shown. FIGS. 3A–F illustrates an h-GF timeline of 0 hour (A), ½ hour (B), 1 hour (C), 3 hour (D), 19 hour (E) and control (F), respectively. Similarly, FIGS. 3G–L illustrates an h-GD timeline of 0 hour (G), ½ hour (H), 1 hour (1), 3 hour (J), 19 hour (K) and control (L), respectively. The partially purified PEH enzyme constituted ~3.2% of the total reaction mixture volume. The Control samples represent 19-hour reaction mixtures that contained the buffer used for the enzyme reconstitution instead of the PEH enzyme. The reaction samples were derivatized prior to GC-FPD chromatography. The retention time ($t_r$) of ca. 4.39 minutes of the derivatized enzymatic reaction products of all the five substrates was similar to that of the derivatized methylphosphonic acid (MPn) standard. The $t_r$ values for derivatized h-GD and h-GF were ca. 6.25 minutes and ca. 8.24 minutes, respectively. (The dotted lines mark the end of the solvent peaks.)

FIG. 6 is similar to FIG. 3, but shows shows PEH degradation of h-VX and h-GB. The timeline of the GC-FPD chromatograms of the PEH reactions at 30° C. with the two (h-VX and h-GB) out of the total of five substrates (ca. 10 mM) and their controls are shown. FIGS. 6A–F illustrates an h-VX timeline of O hour (A), ½ hour (B), 1 hour (C), 3 hour (D), 19 hour (E) and control (F), respectively. Similarly, FIGS. 6G–L illustrates an h-GB timeline of O hour (G), ½ hour (H), 1 hour (1), 3 hour (J), 19 hour (K) and control (L), respectively. The retention time ($t_r$) of ca. 4.39 minutes of the derivatized enzymatic reaction products of all the five substrates was similar to that of the derivatized methylphosphonic acid (MPn) standard. The $t_r$ values for derivatized h-VX and h-GB were ca. 3.61 minutes and ca. 4.04 minutes, respectively. (The dotted lines mark the end of the solvent peaks.)

Figure 7A:
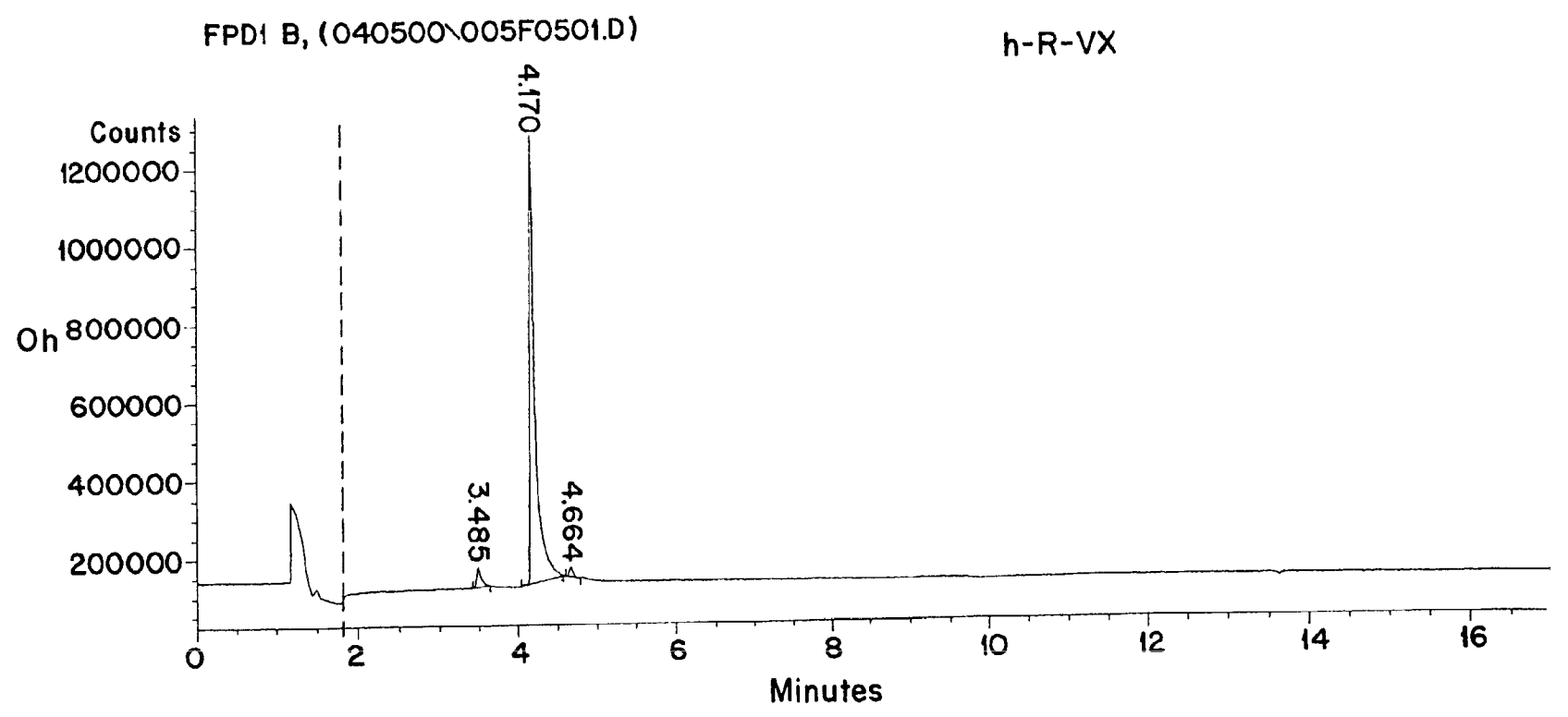
Figure 7B:
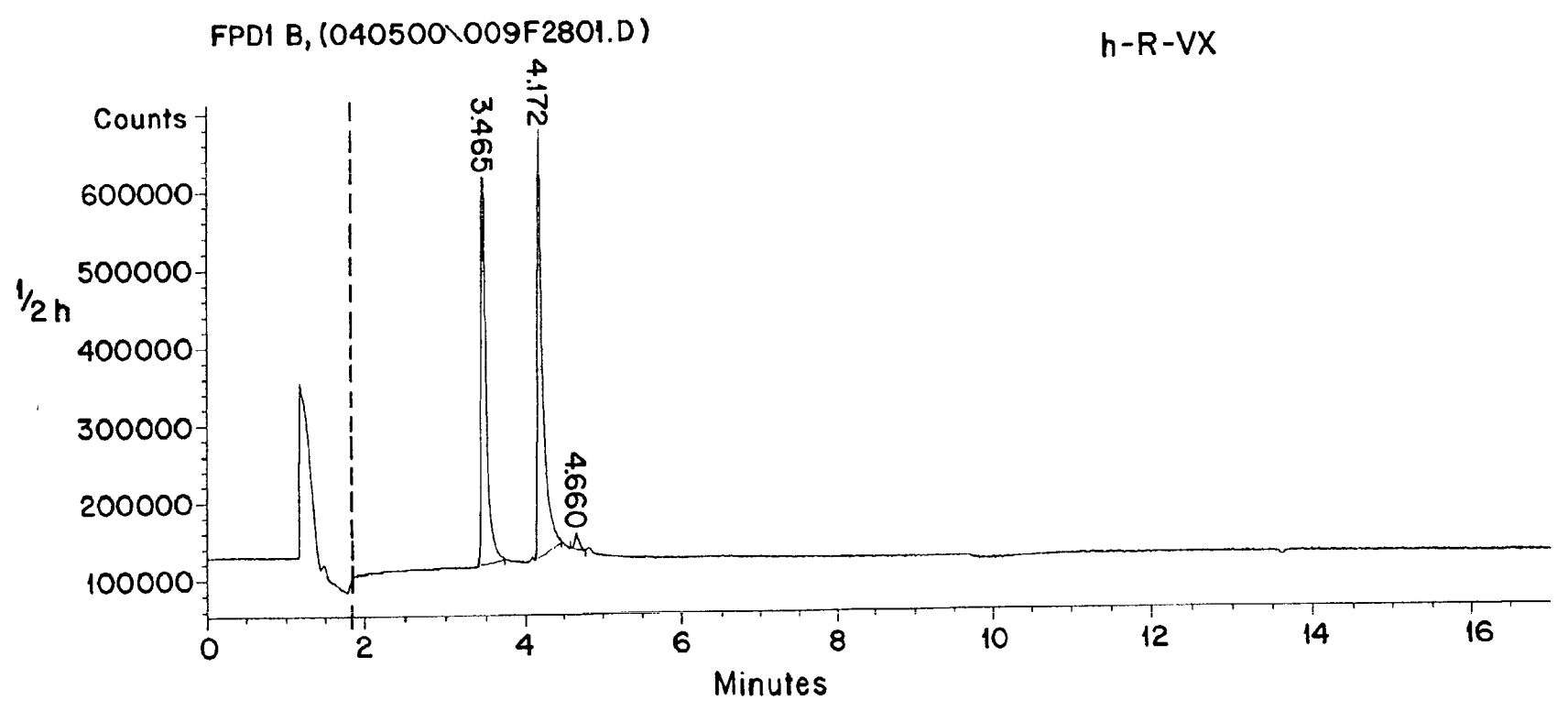
Figure 7F:
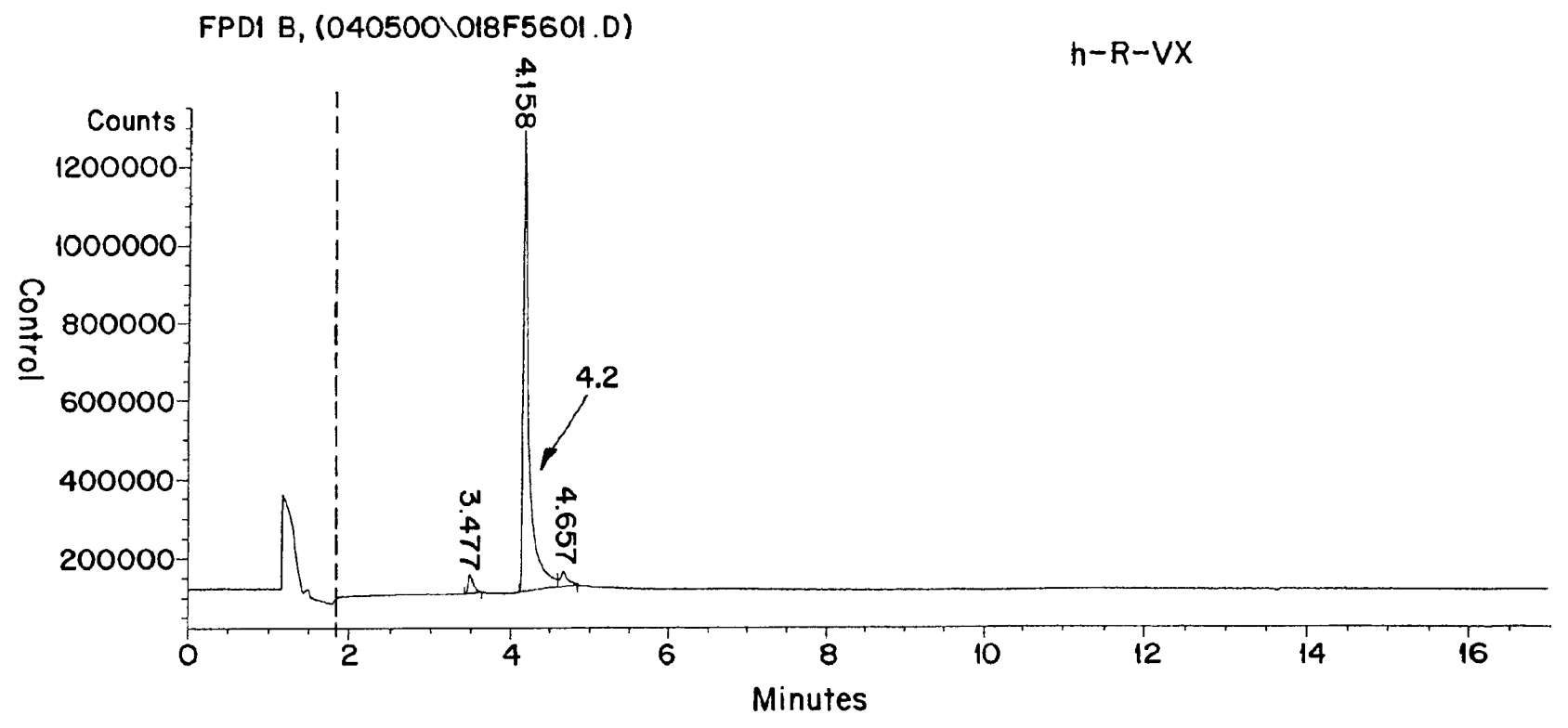

FIG. 7 is similar to FIG. 3, but shows shows PEH degradation of h-R-VX (Russian VX). The timeline of the GC-FPD chromatograms of the PEH reactions at 30° C. with the h-R-VX out of the total of five substrates (ca. 10 mM) and their controls are shown. FIGS. 7A–F illustrates an h-VX timeline of O hour (A), ½ hour (B), 1 hour (C), 3 hour (D), 19 hour (E) and control (F), respectively. The retention time ($t_r$) of ca. 3.46 minutes of the derivatized enzymatic reaction products of all the five substrates was similar to that of the derivatized methylphosphonic acid (MPn) standard. The $t_r$ values for derivatized h-R-VX was ca. 4.20 minutes. (The dotted lines mark the end of the solvent peaks.)

SUMMARY OF THE INVENTION

Figure 1:
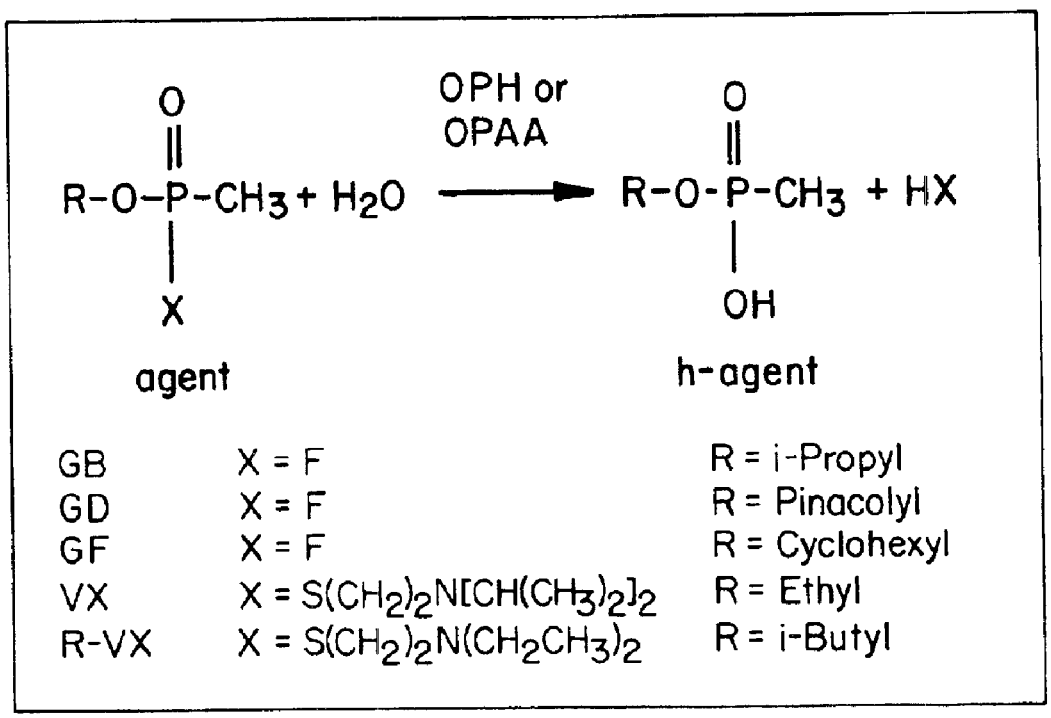
FIG. 1 shows G- and V-agent hydrolysis by OPH or OPAA.

The invention addresses the above-identified problem by the combined use of three enzymes: organophosphorus hydrolase (OPH) and organophosphorus acid anhydrolase (OPAA), and phosphonate ester hydrolase enzyme (PEH). It has recently been found that bacterial phosphonate ester hydrolase enzyme (PEH) selectively degrades esters of alkyl and aryl phosphonates, such as the esters of methyl- and phenyl-phosphonic acids, revealed a new approach to address the above-identified needs. OPH and OPAA both degrade neurotoxic organophosphorus compounds (OP). Thus, the combination of OPH and OPAA with PEH, which further degrades the phospho-products originating from CW agents (e.g., GB, GD, GF, VX, and Russian VX), results in a unique method for analyzing and identifying CW OP.

Employing different combinations of the enzymes generates a unique "fingerprint" from each CW OP. The "fingerprint" consisting of the agent and its products may be analyzed by standard analytical techniques, such as liquid chromatography—mass spectrometry (LC-MS); alternatively, the agent and its derivatized products can be observed by gas chromatography (GC) with a flame photometric detector (FPD) and phosphorus filter. The agent and individual components of these pre-instrumentation derived products can be further interrogated by the existing instrumental methods (e.g., GC-MS, GC-MS/MS) for eventual CW OP identification.

Thus, in one embodiment the invention provides a method of detecting, identifying, and quantifying the presence of chemical warfare agents that contain organophosphorus compounds (such as, for instance, GB, GC, GF, VX and Russian VX), degradation products of such chemical warfare agents, and mixtures thereof, with vastly improved reliability and speed compared to current methodologies. The method is useful to detect and analyze not only known G- and V-agents and their degradation products, but also presently unknown/unclassified CW OP agents.

The method is accomplished by creating a unique agent "fingerprint" through enzymatic sample pre-treatment. In contrast to present methodologies, such as those that utilize cholinesterase, the approach of this invention enables us to generate specific "fingerprints" from the phosphonate ester-containing CW OP neurotoxins through combinatorial application of enzymes of the toxin degradation pathway. The post-treatment analysis of the samples by GC-FPD/MS would produce highly reliable identification and quantification of the known CW OP and would provide sufficient information to greatly reduce the time and effort needed for the identification and quantification of unknown CW OP that contain phosphonate esters.

The invention also provides a simple method for quickly screening incoming samples for the presence of known GB, GD, GF, VX, and Russian VX agents, as well as unknown CW OP agents. Addition of the enzyme mixture (OPH/OPAA/PEH) to each sample enables the conversion of all five neurotoxins to a single methylphosphonate product prior to instrumental analysis. The labile character of the G- and V-type neurotoxins makes it likely that post-exposure samples would already contain considerable amounts of the highly stable phosphonate ester degradation products. This approach enables us to easily identify these degradation phosphonate ester products, important biomarkers for both known and prospective CW OP neurotoxins that are based on these esters. In addition, with all of the embodiments of this invention it is possible to detect, identify, and quantify other phosphonate ester degradation products besides methylphosphonate, including compounds having an alkyl or aryl substitution to the $CH_3$ in the above-described Formula I (for example, ethylphosphonate, which is present in nerve agents such as VE (O-Ethyl-S-[2-(diethylamino)ethyl]ethylphosphonothioate), or phenylphosphonate).

In one broad embodiment of this invention, it is possible to use PEH alone, which method would include the steps of:

(a) contacting a liquid sample suspected of containing chemical warfare agents that contain organophosphorus compounds, degradation products, chemical warfare agent precursors, and mixtures thereof, with a sufficient amount of an alkaline substance (such as, for instance, sodium or potassium or ammonium hydroxide, or any appropriate alkali, including a high pH buffer) and time, to convert all of the agent to its corresponding phosphonate ester, (b) neutralizing the solution of step (a) using known protocols (such as, for instance by titration with hydrochloric acid, and/or by adding a buffer to bring the resulting solution to the desired pH), and (c) treating the solution of step (b) with a sufficient amount of phosphonate ester hydrolase (PEH) and time, to convert all or most of the phosphonate ester to its corresponding phosphonate, (d) detecting the presence of phosphonate, especially methylphosphonate (or other alkylphosphonates, as applicable), which presence is indicative of chemical warfare agents that contain organophosphorus compounds. Preferably, the degradation product methylphosphonate (or other alkylphosphonates, as applicable) may be detected using liquid or gas chromatography, mass spectrometry, flame photometric detector and phosphorus filter, or any combination of these techniques. Preferably, the amount of phosphonate ester hydrolase used is at least about 0.5 EMPA units per ml. It is noted that one EMPA unit will hydrolyze 1.0 micromole of ethyl methylphosphonate (EMPA) per minute.

In another broad form of the invention, this method includes the steps of:
  (a) contacting a liquid sample suspected of containing chemical warfare agents that contain organophosphorus compounds, degradation products, chemical warfare agent precursors, and mixtures thereof, with a sufficient amount of phosphonate ester hydrolase (PEH), a sufficient amount of organophosphorus hydrolase (OPH) and a sufficient amount of a organophosphorus acid anhydrolase (OPAA) in a buffered aqueous solution, and allowing sufficient time for the enzymes to hydrolyze all or most of the substrates,
  (b) detecting the presence of phosponate, especially methylphosphonate (or other alkylphosphonates, as applicable), which presence is indicative of chemical warfare agents that contain organophosphorus compounds. Preferably, the degradation product phosphonate may be detected using liquid or gas chromatography, mass spectrometry, flame photometric detector and phosphorus filter, or any combination of these techniques.

Preferably, the amount of phosphonate ester hydrolase used is at least about 0.5 EMPA units per ml. Preferably, the amount of organophosphorus hydrolase used is at least about 25 DFP units per ml. Preferably, the amount of organophosphorus acid anhydrolase used is at least about 25 DFP units per ml. It is noted that one EMPA unit will hydrolyze 1.0 micromole of ethyl methylphosphonate (EMPA) per minute. Similarly, one DFP unit will hydrolyze 1.0 micromole of diisopropyl fluorophosphate (DFP) per minute.

For example, to quickly screen large amounts of samples to determine the presence of nerve agents, it is possible to use one of the two above-described methods, in a buffered solution (e.g., (1) PEH alone, with alkali plus neutralization, or (2) all three enzymes are combined together in a buffered aqueous solution). If an OP neurotoxin is present in the sample, the enzyme(s) will generate methylphosphonate (or other alkylphosphonates, as applicable). Following this, optionally, one of several further tests may be carried out to identify and quantify the OP neurotoxin. For example, all three enzymes may be employed again in a different manner, where four aliquots of the sample are analyzed as follows: one aliquot contains only the untreated sample; a second aliquot contains the sample plus OPH and OPAA; a third aliquot contains only PEH; and a fourth aliquot contains OPH, OPAA, and PEH. After allowing sufficient time for the enzymes to hydrolyze all or most of the substrates in a buffered aqueous solution, the first aliquot containing only the untreated sample may be analyzed by gas chromatography in two capacities—without derivatization and after being derivatized. The other three aliquots may be analyzed by gas chromatography after derivatization. All results of all four aliquots are then compared to each other and to standards, and the peaks from the gas chromatography analysis will indicate the identity and quantity of the particular nerve agent (or its degradation products) in the sample.

Another way to identify and quantify the OP neurotoxin is to employ an alkali and PEH. The only enzyme employed in this particular method is PEH, which is useful when the sample contains VX, since OPAA does not degrade VX and OPH does so minimally. For instance, four aliquots of the sample are analyzed as follows: one aliquot contains only the untreated sample; a second aliquot contains the sample plus alkali so that this sample solution is neutralized (e.g., treated with 1/10 volume of 10 N NaOH for 1 hour and neutralized with 1/10 volume of 10 N acid); a third aliquot contains only PEH; and a fourth aliquot contains a part of the sample contained in the second aliquot following neutralization, plus PEH. After allowing sufficient time for the enzymes to hydrolyze all or most of the substrates in a buffered aqueous solution, the first aliquot containing only the untreated sample may be analyzed by gas chromatography in two capacities—without derivatization and after being derivatized. The other three aliquots may be analyzed by gas chromatography after derivatization and the results are then compared. The peaks from the gas chromatography analysis will indicate additional specificity about the particular nerve agent in the sample.

In a related embodiment, the invention contemplates a gas chromatography-flame photometric detector/mass spectrometry (GC-FPD/MS) methodology that would facilitate the reliability and speed for detection, identification, and quantification of known and unknown CW OP neurotoxins with phosphonate ester moieties and their degraded phospho-products.

The sample to be tested is preferably in the form of a solution. In one aspect of the invention, the solution is obtained by wiping a suspected surface with a polyester or similar type wipe or cloth and thereafter extracting the materials present on the wipe with a aqueous buffer solution such as 5 mM Bis Tris Propane, pH 7.0. Alternatively, a soil sample can be eluted to obtain the liquid sample for analysis. A still further aspect includes treating an aliquot of an organic solvent including a sample suspected of containing the CWA analyte with an alkali for a sufficient time (such as, for instance, about one hour) and subsequently evaporating the organic solvent and neutralizing the remaining aqueous solution with an acid to obtain hydrolyzed derivative of the CWA analyte believed to be therein.

In another embodiment of the invention there is provided kits for detecting the presence of chemical warfare agents that contain organophosphorus compounds, precursors of chemical warfare agents, and degradation products thereof. One such kit includes, packaged in association:
  (a) phosphonate ester hydrolase (preferably at least about 0.5 EMPA units), an alkali, and a neutralizing agent, and
  (b) a detection device for detecting the presence of phosphonate, especially methylphosphonate (or other alkylphosphonates, as applicable) which presence is indicative of chemical warfare agents that contain organophosphorus compounds.

Another such kit includes, packaged in association:
  (a) phosphonate ester hydrolase (preferably at least about 0.5 EMPA units), organophosphorus hydrolase (preferably at least about 25 DFP units), and organophosphorus acid anhydrolase (preferably at least about 25 DFP units); and
  a detection device for detecting the presence of phosphonate, especially methylphosphonate (or otheralkylphosphonates, as applicable) which presence is indicative of chemical warfare agents that contain organophosphorus compounds.

Advantages of these kits, and indeed all of the embodiments of this invention, are its tremendous reliability utilizing the specificity of these enzymes.

In a further embodiment, the invention provides a novel composition capable of degrading chemical warfare agents and/or their degradation products. The composition comprises phosphonate ester hydrolase (preferably at least about 0.5 EMPA units), organophosphorus hydrolase (preferably at least about 25 DFP units), and organophosphorus acid anhydrolase (preferably at least about 25 DFP units).

When desirable, a chromogenic detector reagent may be used with the compositions, methods of detection and kits of this invention.

DETAILED DESCRIPTION OF THE PREFERRED EMBODIMENTS

This invention augments existing chemical warfare agent detection methods and is based on a novel generic method that is predicated by the specificity of PEH to degrade the products of the agents. The method can be used for both initial screening and identification purposes with vastly improved efficiency and reliability. The methods, kits and compositions of this invention would be suitable for many applications, both military and civilian. It would be especially well suited for Chemical Weapons Convention (CWC) verification purposes, where the highest degree of reliability is required and both the allotted time and the allowed equipment are very limited. In this regard, the proposed method could be applicable for Domestic Preparedness and Homeland Defense Programs as well.

By making use of the specificity of certain enzymes—PEH alone, or a combination of OPH, OPAA and PEH—our invention is able to facilitate the identification and quantification of both known and unknown CW OP compounds based on aryl- and alkyl-phosphonate esters and their degradation phospho-products. OPH is similar to OPAA in activity. Both enzymes act on CW agents and other OPs with tri-substituted phosphorus (e.g. pesticides), whereas PEH acts on the degradation products from CW agents. Combined action of these enzymes would generate aryl- or alkyl-phosphonic acids (that is, a single methylphosphonic acid (MPn) from the OP nerve agents—GB, GD, GF, VX, and Russian VX) and therefore greatly reduce the number of initial analytes needed for screening purposes.

As noted above CWOP agents undergo a slow spontaneous hydrolysis producing very stable methylphosphonate esters as the major phospho-products. OPH (see references 1–3, listed below) and OPAA (see references 4–9) catalytically degrade neurotoxic organophosphorus compounds (OP), but they act on both pesticides and CW OP. FIG. 1 depicts OPH and OPAA hydrolysis of five selected CW OP. The enzymes convert the agents to their respective methylphosphonate esters as the sole phospho-products (see references 1–9). Alkali treatment of these agents results in similar conversions.

The PEH enzyme effectively degrades hydrolyzed agents GB, GD, GF, VX, and Russian VX (R-VX) (FIG. 2) (See references 10 and 11).

Figure 2:
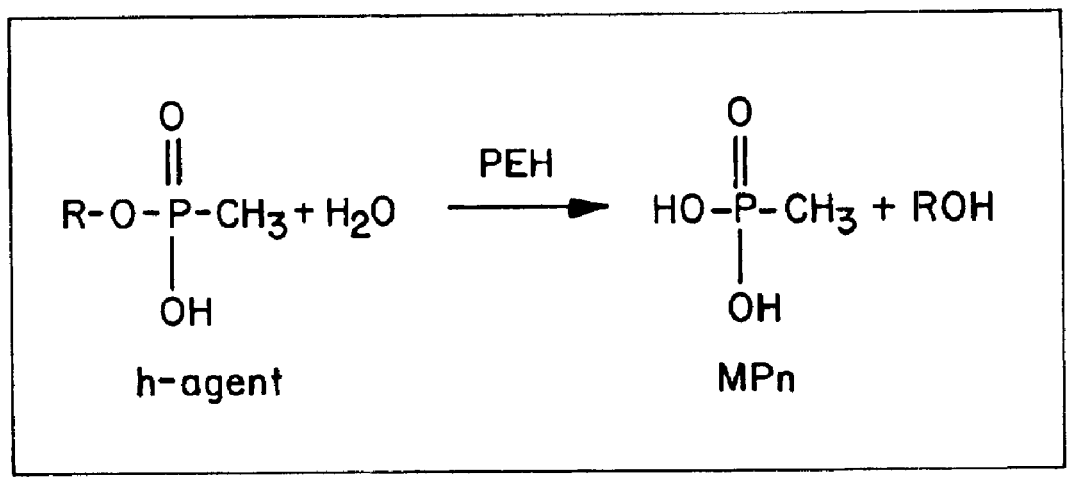
FIG. 2 shows PEH degradation of hydrolyzed agents.
Figure 3A:
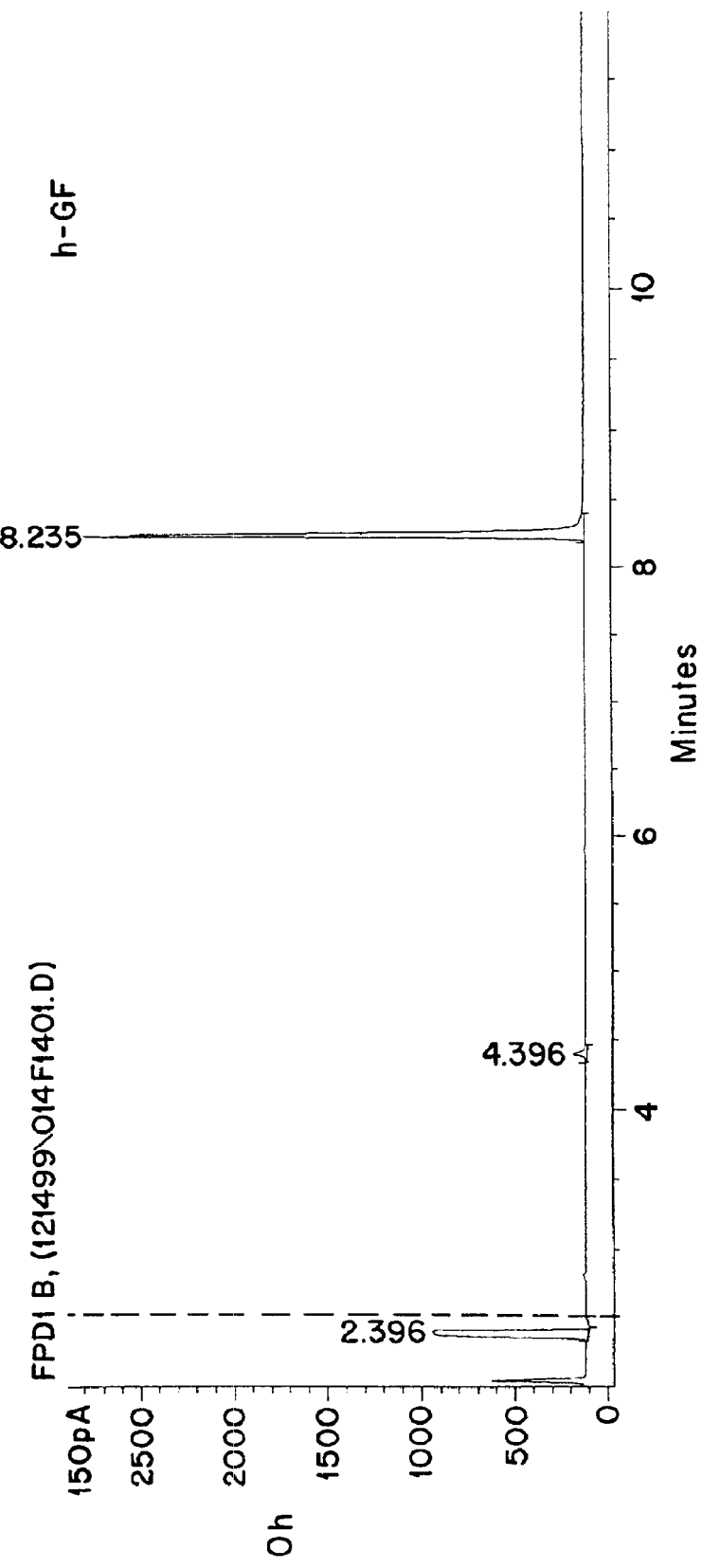
Figure 3B:
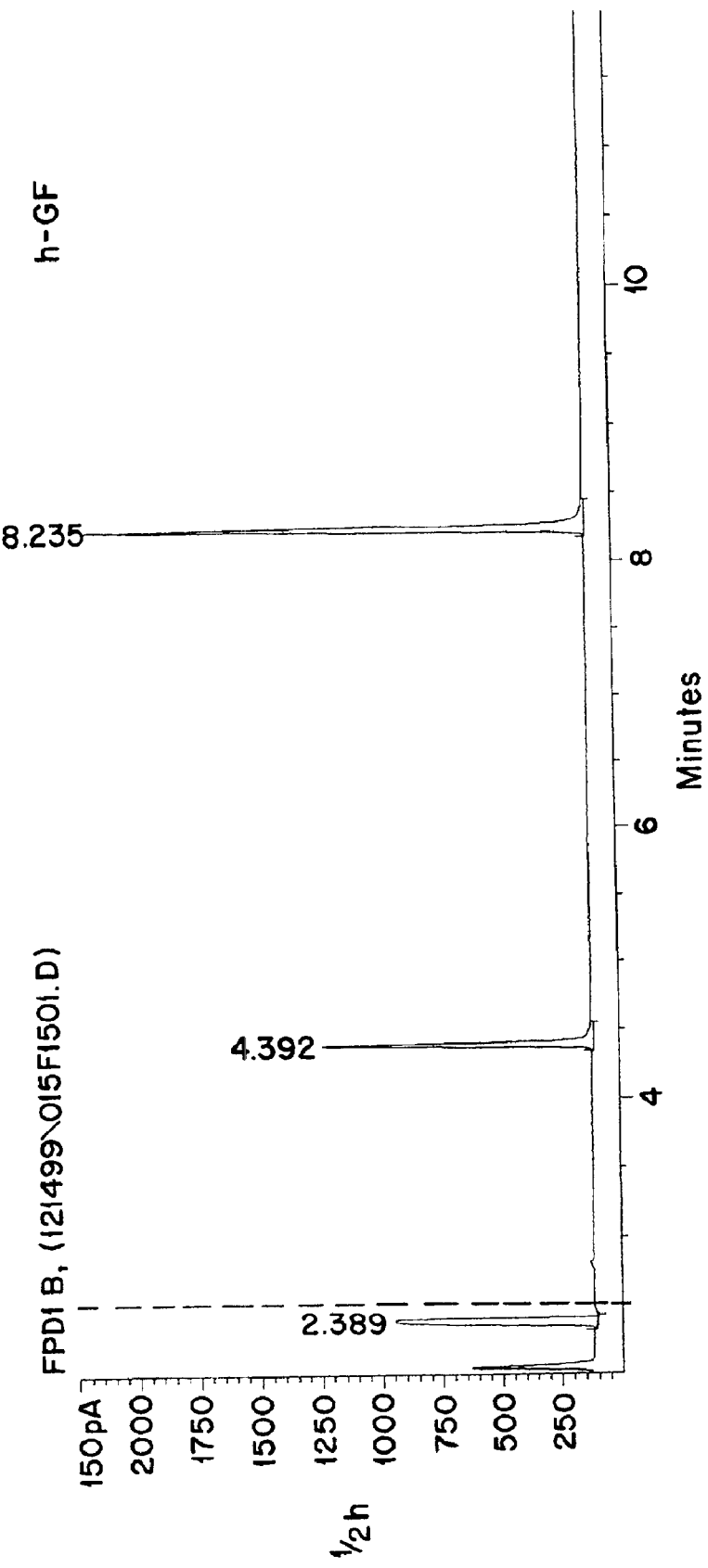
Figure 3C:
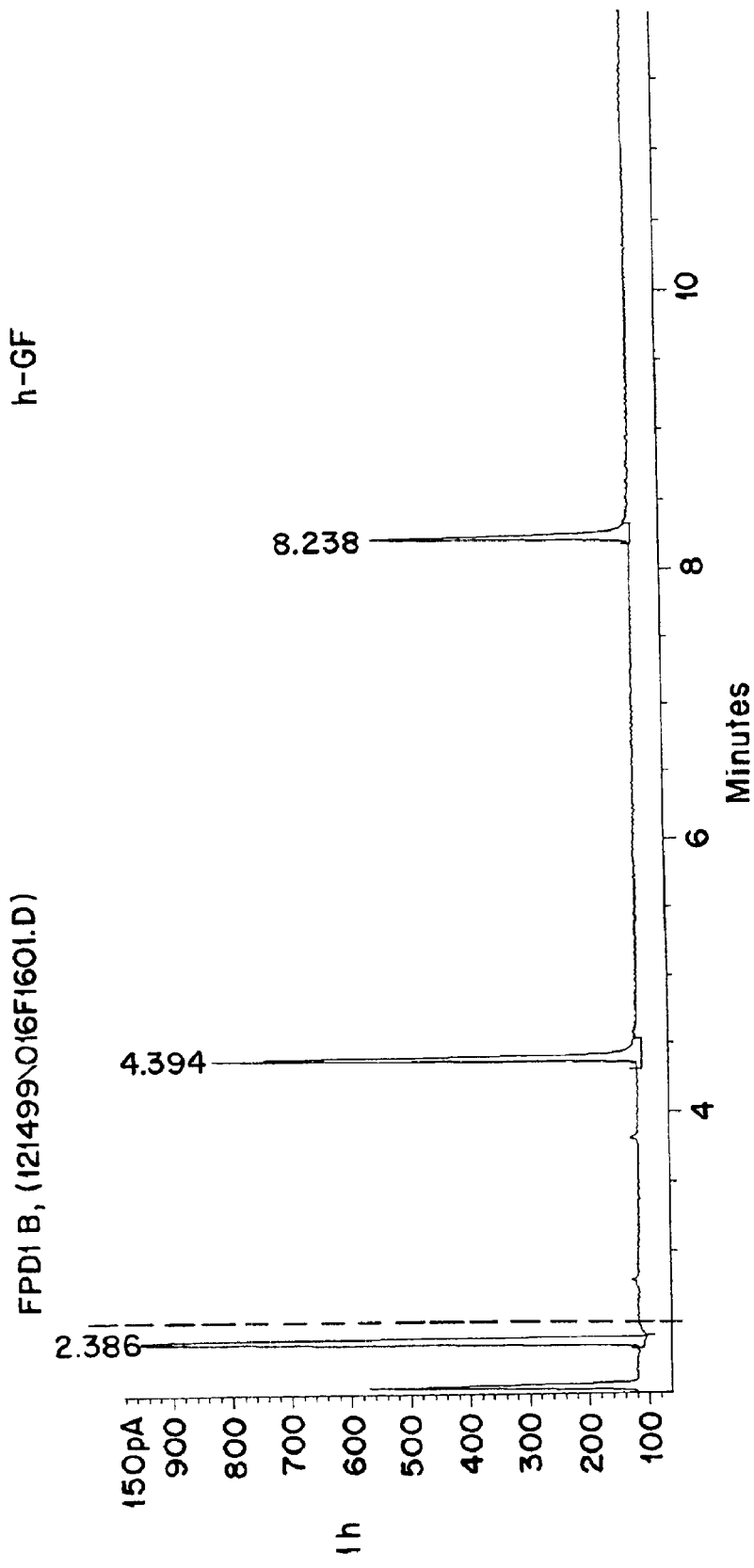
Figure 3E:
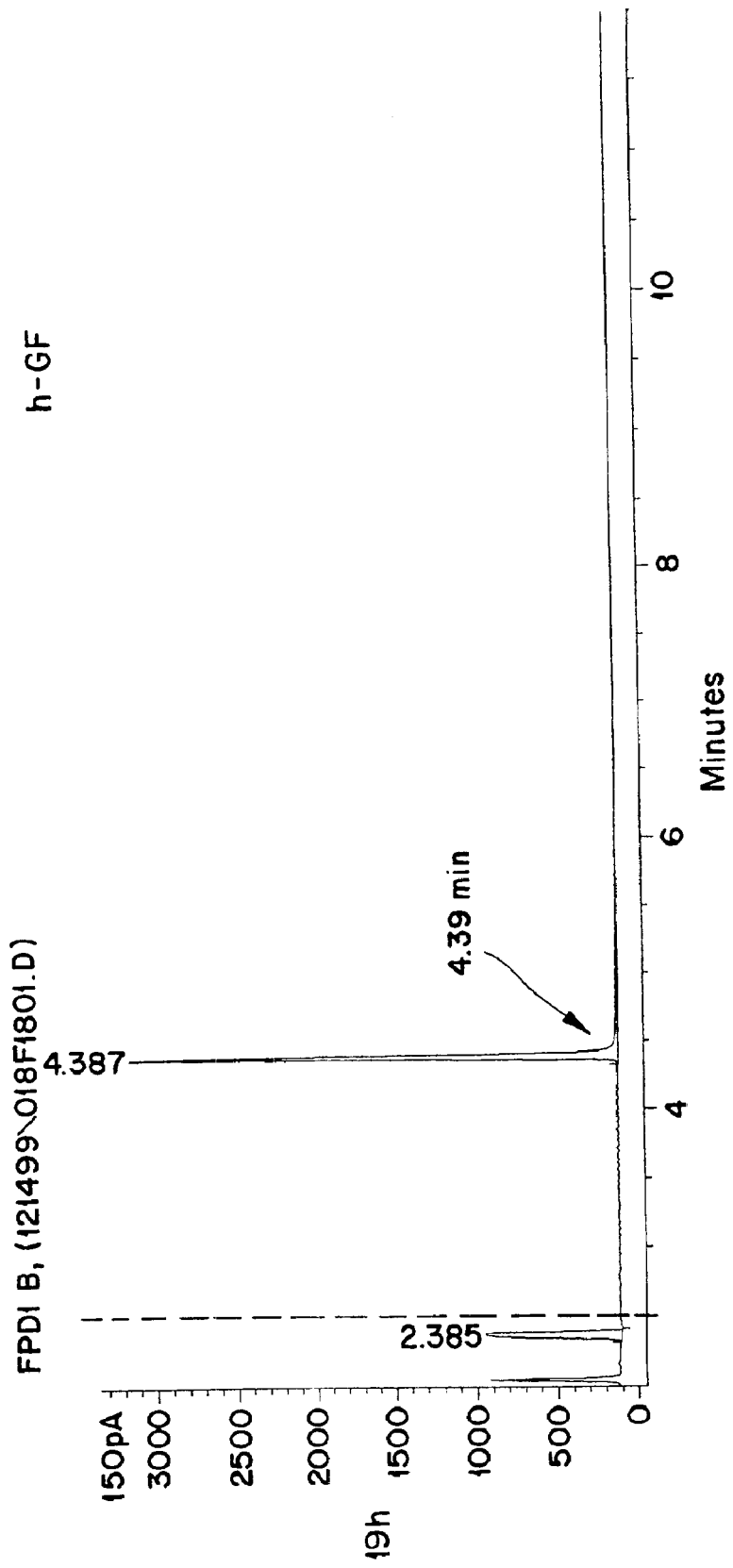
Figure 3F:
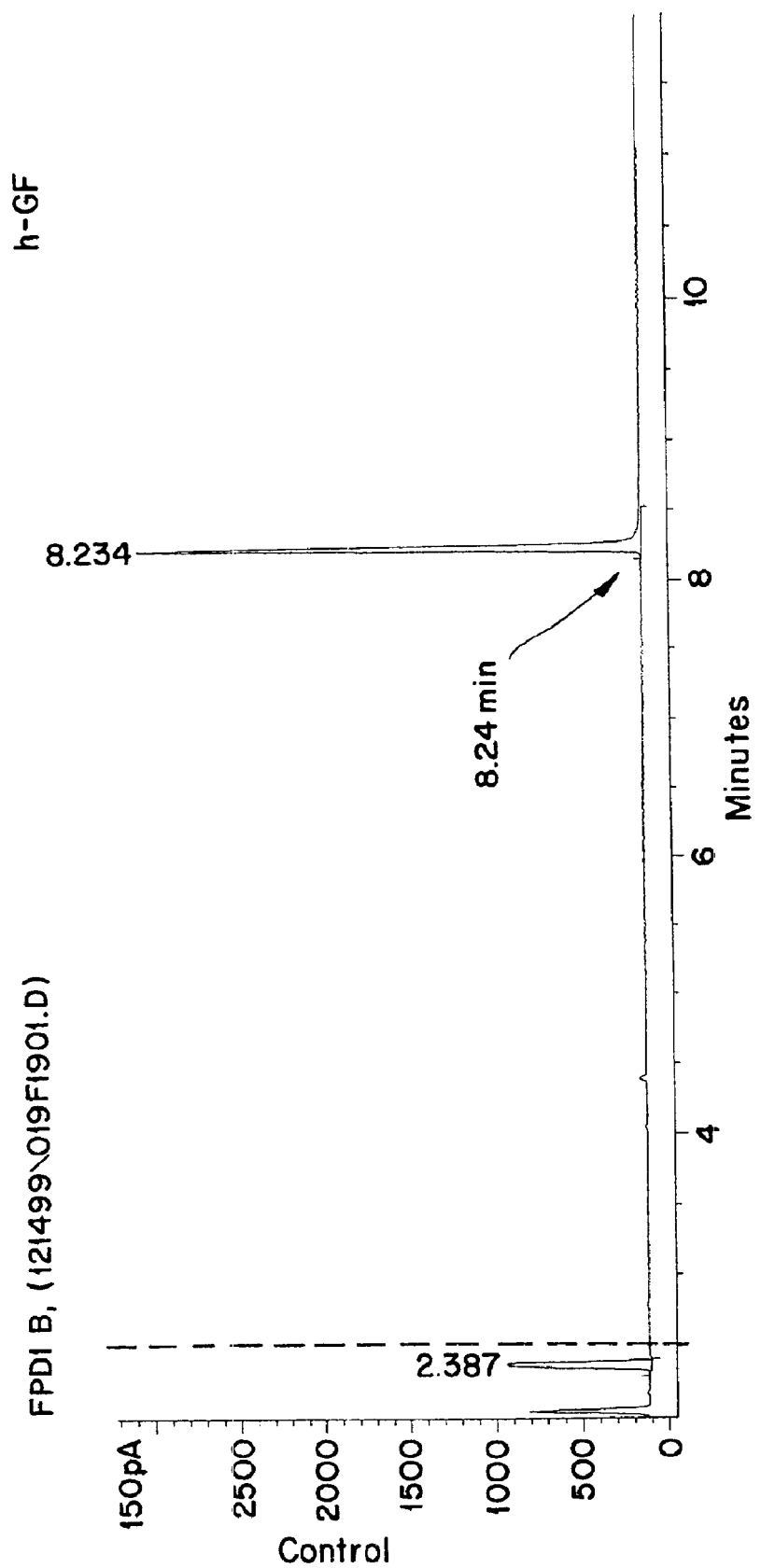
Figure 3G:
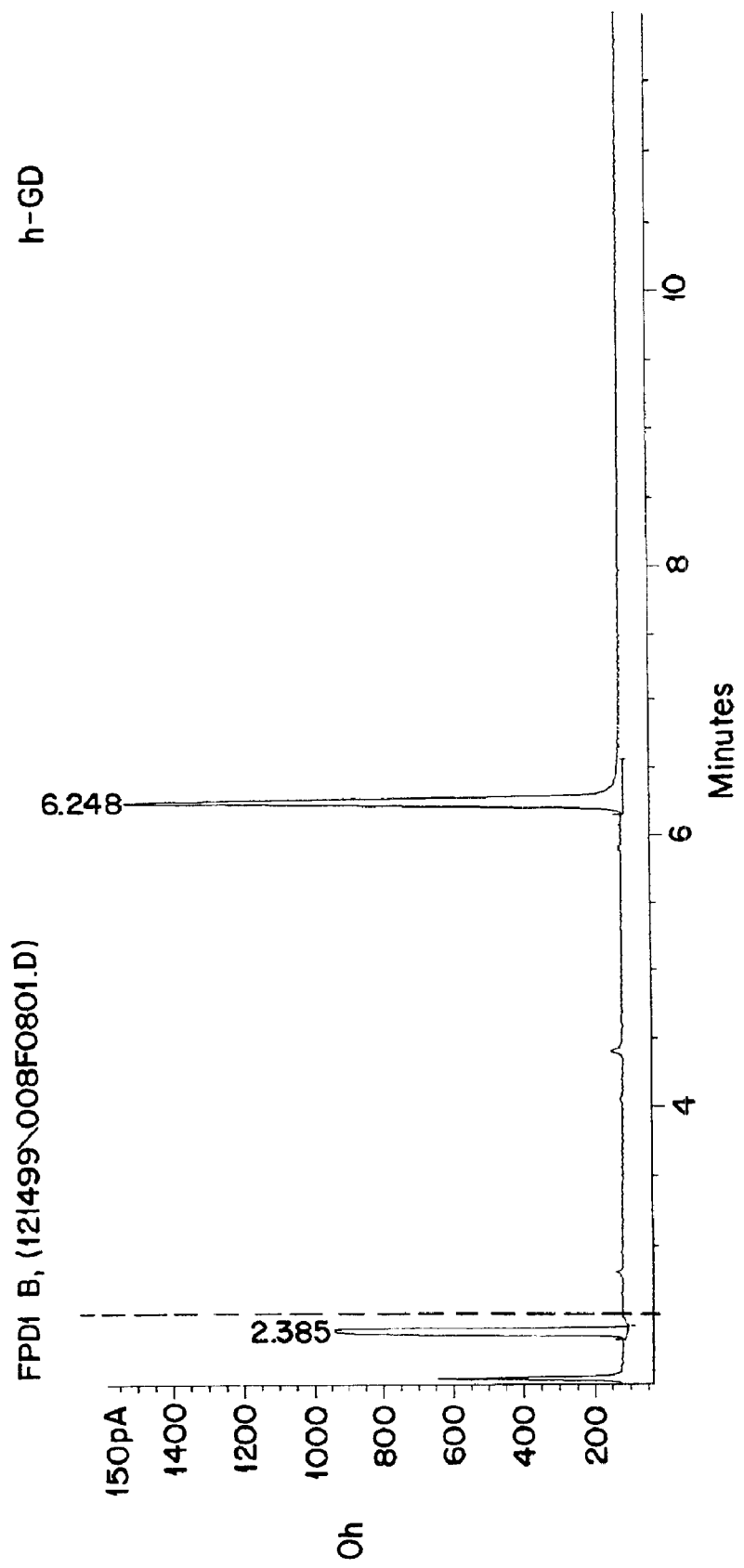
Figure 3H:
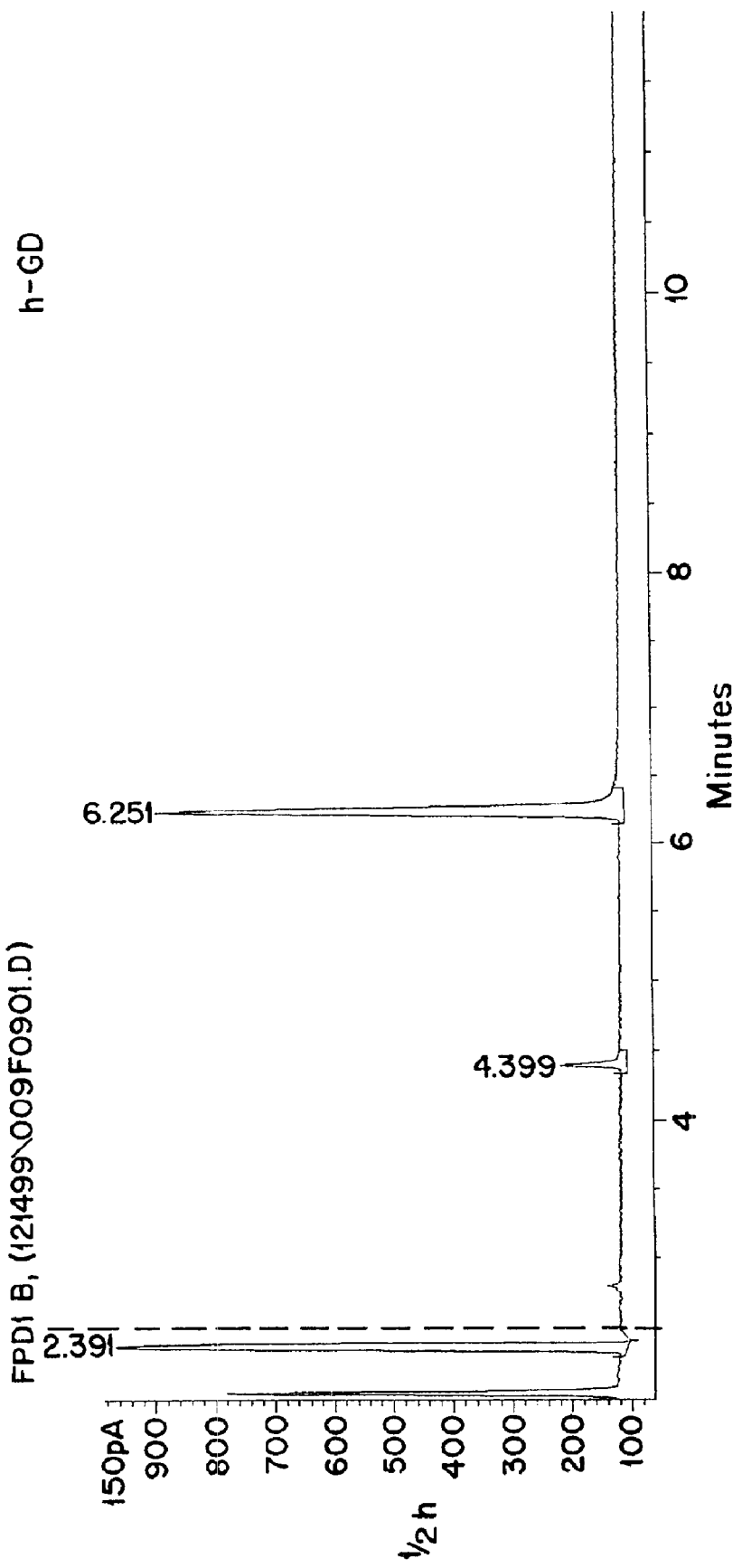
Figure 31:
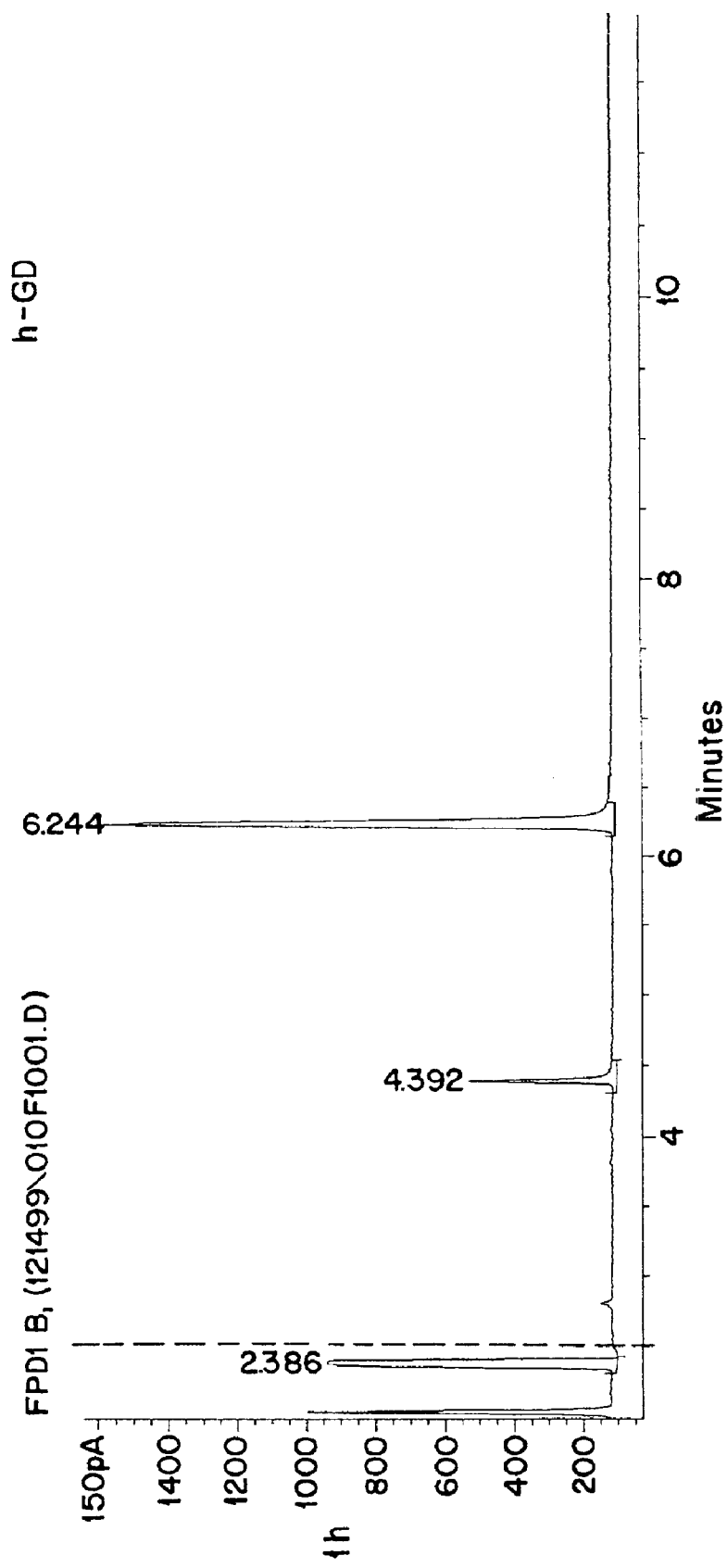
Figure 3J:
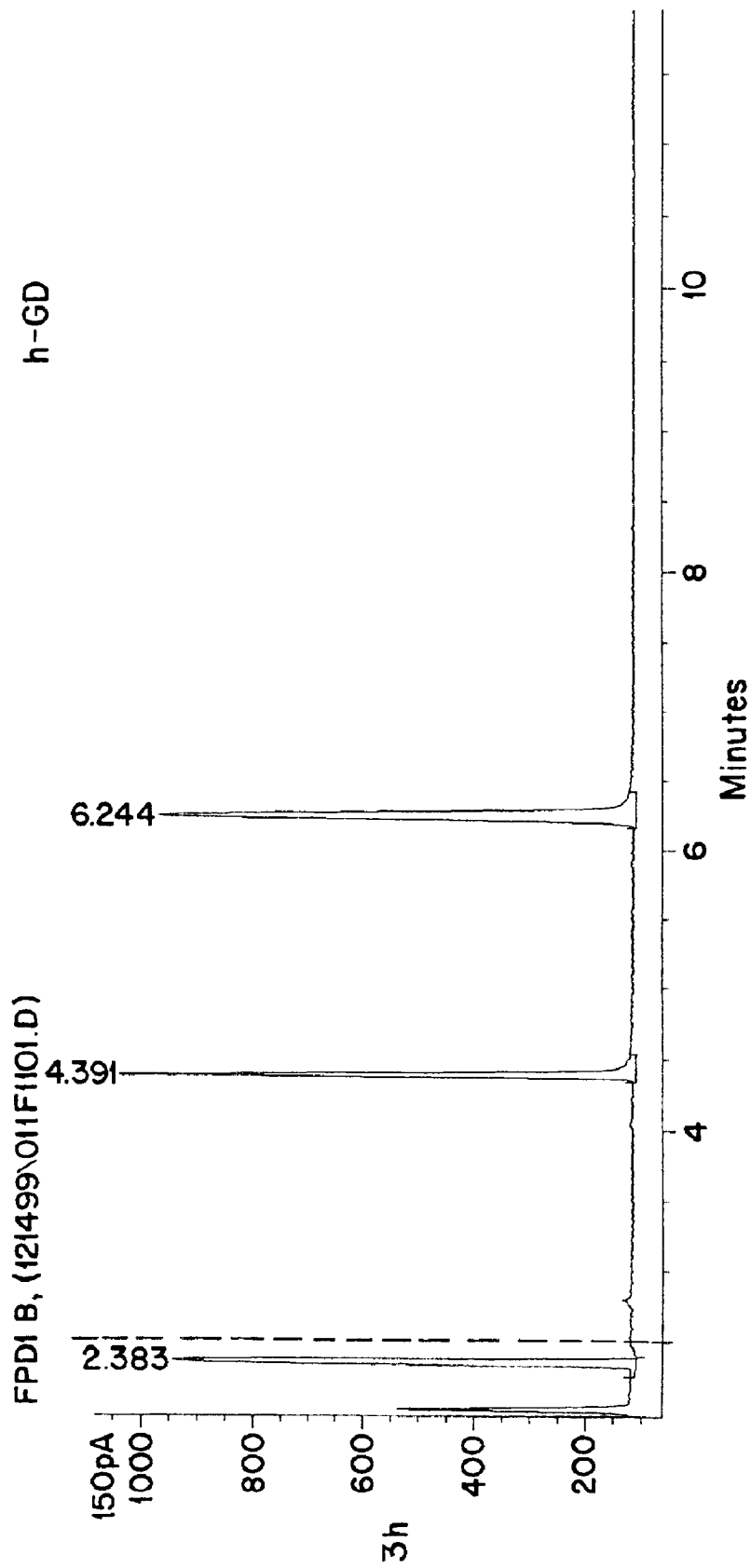
Figure 3K:
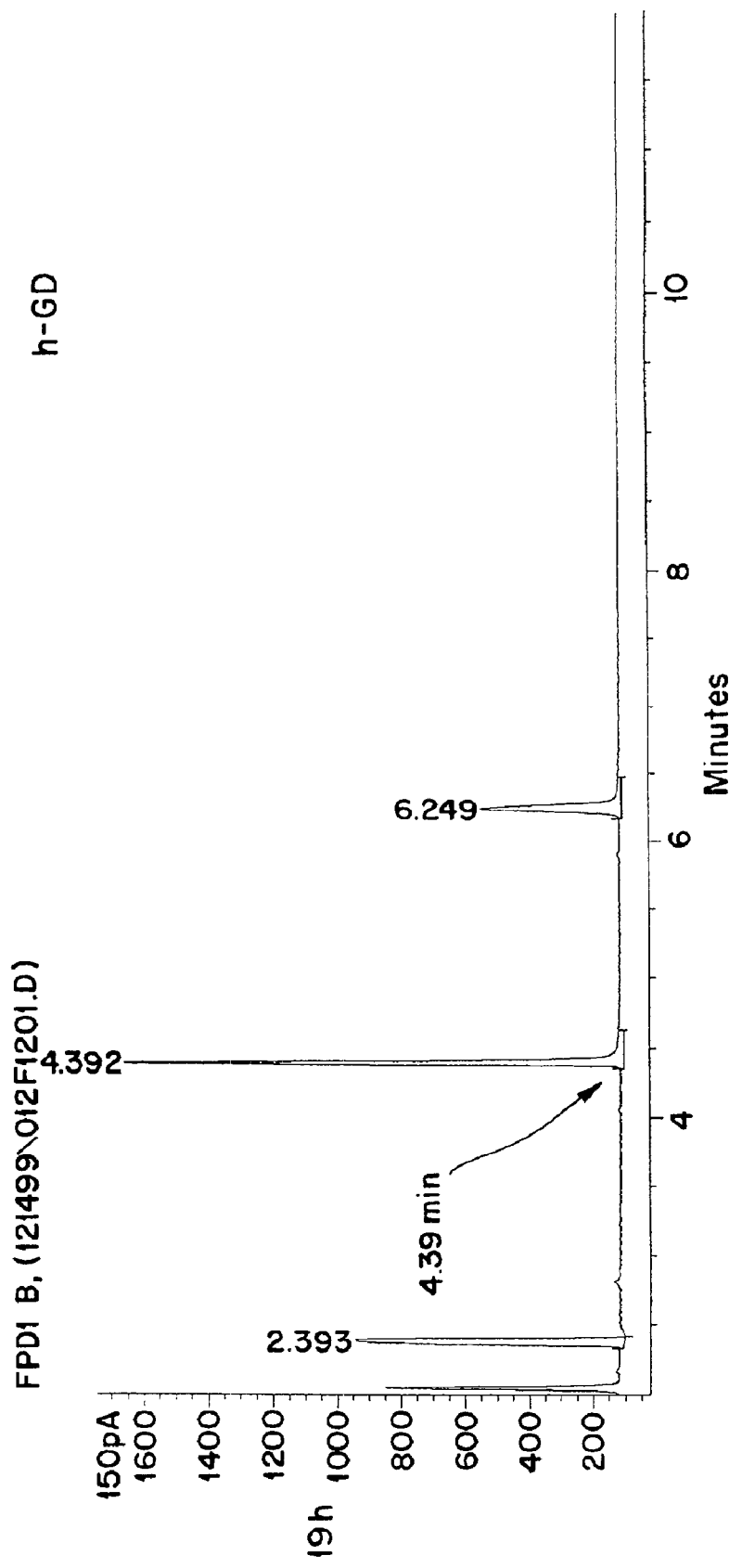
Figure 3L:
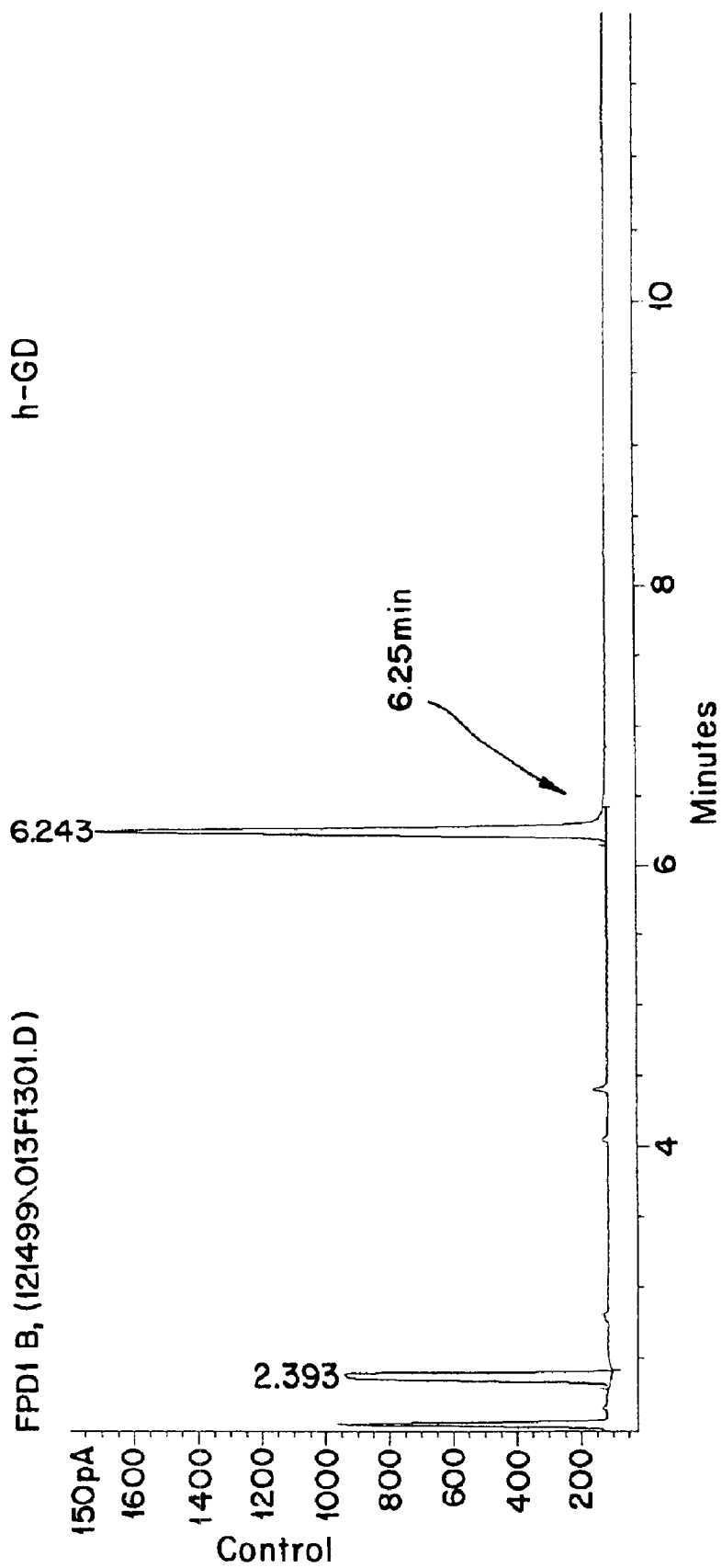
Figure 4:
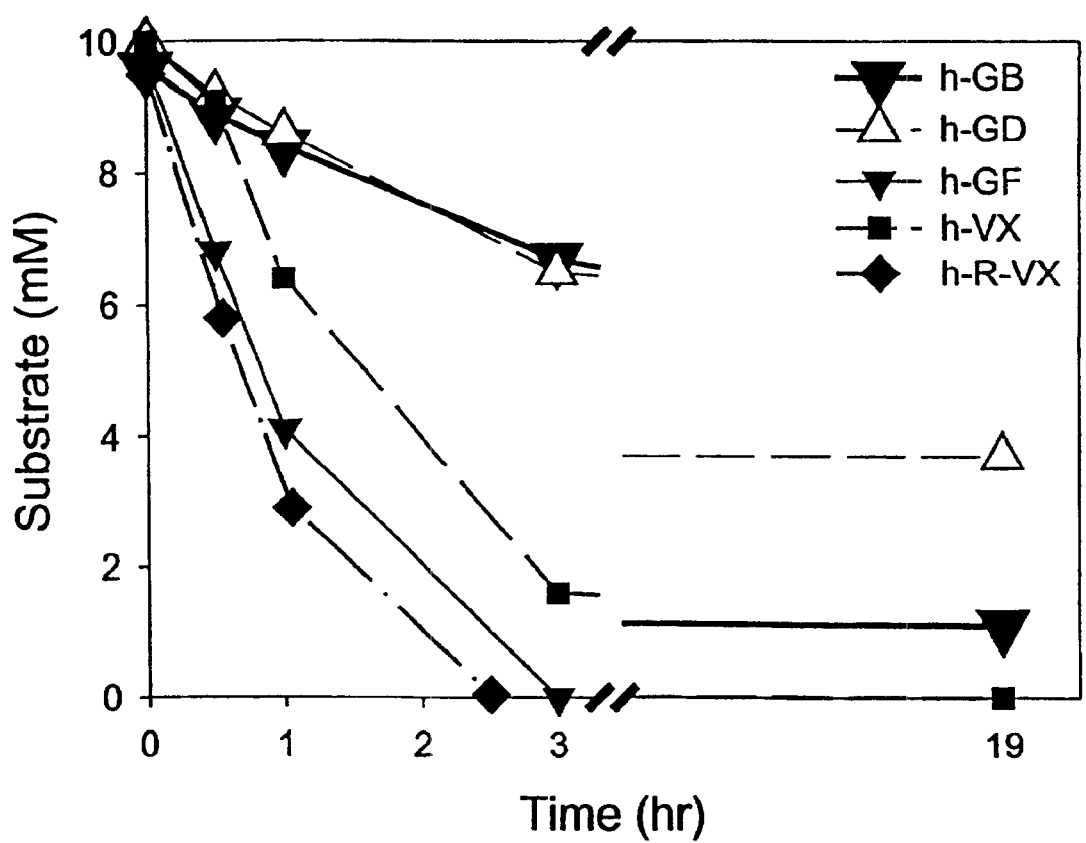
FIG. 4 illustrates PEH degradation of hydrolyzed agents. The five substrates h-GB, h-GD, h-GF, h-VX and h-R-VX were incubated at 30° C. with and without PEH enzyme as in FIG. 3. No detectable degradation product was observed for any of the five substrates after 19 hours of incubation in controls without the PEH enzyme.

The PEH enzyme was used against the alkaline hydrolysis products of the agents. Five agents—GB, GD, GF, VX, and Russian VX (R-VX)—were hydrolyzed in a four percent sodium hydroxide solution for two days and titrated to neutral pH. The results obtained with the hydrolyzed agents—h-GB, h-GD, and h-VX—were compared with the corresponding commercially obtained compounds—isopropyl methylphosphonate (IMPn), pinacolyl methylphosphonate (PMPn), and Ethyl methylphosphonate (EMPn). No significant differences were found between the respective compounds as judged by the analysis of the derivatized samples on GC-FPD. This experiment confirmed that the agents completely hydrolyze to their respective methylphosphonate esters under these conditions. The hydrolyzed agents were incubated at 10 mM initial concentrations with and without the PEH enzyme in 50 mM Bis Tris Propane, pH 8.5, 1 mM $MnCl_2$. In order to allow a better observation of the enzyme kinetics, partially purified PEH was used in relatively small quantities (ca. 3.2% of the total reaction volume). At appropriate intervals, aliquots were withdrawn and quenched. The samples were dried, sililated, and analyzed on GC-FPD. FIG. 3 shows the PEH degradation timelines of two representative hydrolyzed CW agent substrates on GC-FPD chromatograms. The figure demonstrates that PEH degraded hydrolyzed GF (h-GF) more efficiently than hydrolyzed GD (h-GD). PEH converted all five hydrolyzed agents to methylphosphonic acid (MPn) and the respective alcohol (FIG. 2). Overall PEH degradation rates for the five hydrolyzed agent substrates were observed as follows h-R-VX>h-GF>h-VX>h-GB>h-GD (FIG. 4) (See references 10 and 11).

PEH was also tested against two chromogenic substrates. Chromogenic substrates are helpful to track PEH enzymatic activity. The release of the yellow p-nitrophenol product, which was monitored spectrophotometrically, from both substrates by the enzymatic reaction, indicated that PEH was effective in degrading both p-nitrophenyl phenylphosphonate and p-nitrophenyl methylphosphonate. Thus, the breakdown of these substrates by PEH is easily detected as they produce colored (yellow) product, which can be monitored spectrophotometrically without the need of derivatization and GC. Therefore, it can be very useful to select fractions of interest for further analysis during the enzyme purification.

The experiments demonstrate that PEH enzyme specifically degrades the aryl and alkyl esters of aryl- and alkylphosphonates. The GB, GD, GF, VX, and Russian VX nerve agents are all based on alkyl esters of alkylphosphonates (alkyl methylphosphonate esters). Germane to this is the specificity exhibited by PEH against the products of the current and prospective CW OP nerve agents. Known CWAs may be degraded with OPH/OPAA and OPH/OPAA/PEH enzyme preparations and subsequently the differences in characteristics of the untreated agents and their degraded products may be compared to ascertain the identities of the agents. For the initial analysis, we selected the differences in the retention times ($t_r$) on GC-FPD as the discriminating parameter. (We considered that the utilization of GC-PFPD could provide better sensitivity than GC-FPD.)

Table 1 shows the retention times of the five selected agents and their sililated degradation products in our experiments. The retention times ($t_r$) of these agents are markedly different on GC. Digestion of these agents with OPH/OPAA/PEH (or alternatively alkali/neutralization/PEH) yields methylphosphonic acid (MPn) as the sole end-product upon GC-FPD analysis, whereas digestion performed by OPH/OPAA (or alternatively alkali) alone yielded the respective methyl phosphonate esters (MPE) instead. The five methyl phosphonate esters (MPE) obtained from the five CW OP differ markedly in their $t_r$ values. Taken together, these results suggest that the identification and quantification of CW OP can be readily accomplished by analyzing the "fingerprint" patterns obtained upon treating portions of the sample with three separate enzyme preparations—PEH, OPH/OPAA/PEH and OPH/OPAA. Similar analytical results could be obtained by treating the sample with the alternate set of three preparations—PEH, alkali/neutralization/PEH, and alkali/neutralization (or alkali alone). It is noted that the neutralization step is necessary only prior to the enzymatic treatment step in order to allow the enzyme activity in the appropriate pH range. Comparing the analytical results amongst these preparations between each other and to the database values would provide the necessary information for the identification and quantification of CW OP and its products. For example, the analytical results from GC-FPD retention time ($t_r$) values of the peaks would enable the identification, whereas the areas under the curve (AUC) of the peaks would enable the quantification of CW OP and its products. In order to verify the proposed scheme and obtain definitive identification, initial results may be supplemented by confirmatory analysis. GC-MS analysis is the most suitable tool for this purpose. Therefore, for example, a database may be created by simultaneously monitoring FPD and MS signals on GC.

TABLE 1

The retention times of the agents and their silylated products on GC-FPD.

| | $t_r$ Values (ca. min) | | |
|---|---|---|---|
| AGENT | Agent | MPE | MPn |
| GB | 4.9 | 4.0 | 4.4 |
| GD | 7.5 | 6.3 | 4.4 |
| GF | 9.2 | 8.2 | 4.4 |
| VX | 9.9 | 3.8 | 4.4 |
| R-VX | 9.7 | 4.7 | 4.4 |

(Note: As would be readily apparent to someone having ordinary skill in this art, the retention times in Table 1 correspond to the GC setup utilized by the inventors, and may vary from another GC apparatus depending on conditions (e.g., column type and dimensions, oven temperature regime, and flow rates of carrier gases). However, forgiven set-up parameters the retention times are very consistent.)

Figure 5A:
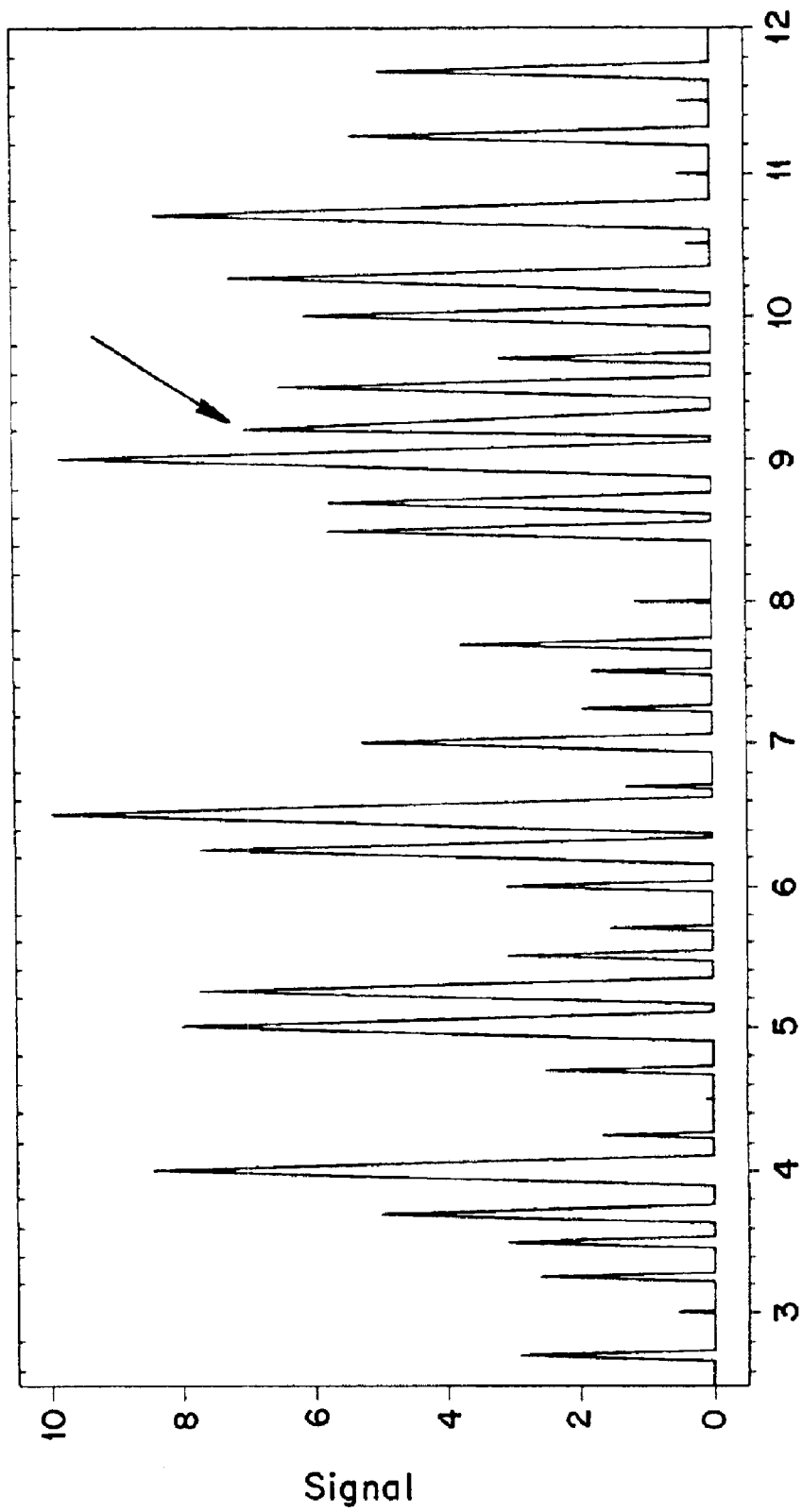
FIG. 5 represents the anticipated GC-FPD chromatograms of a hypothetical sample containing GF agent and non-CW phospho-compounds before and after enzymatic treatment: a) untreated sample (FIG. 5A), b) after OPH/OPAA, (FIG. 5B), and c) after OPH/OPAA and PEH (FIG. 5C).
Figure 5B:
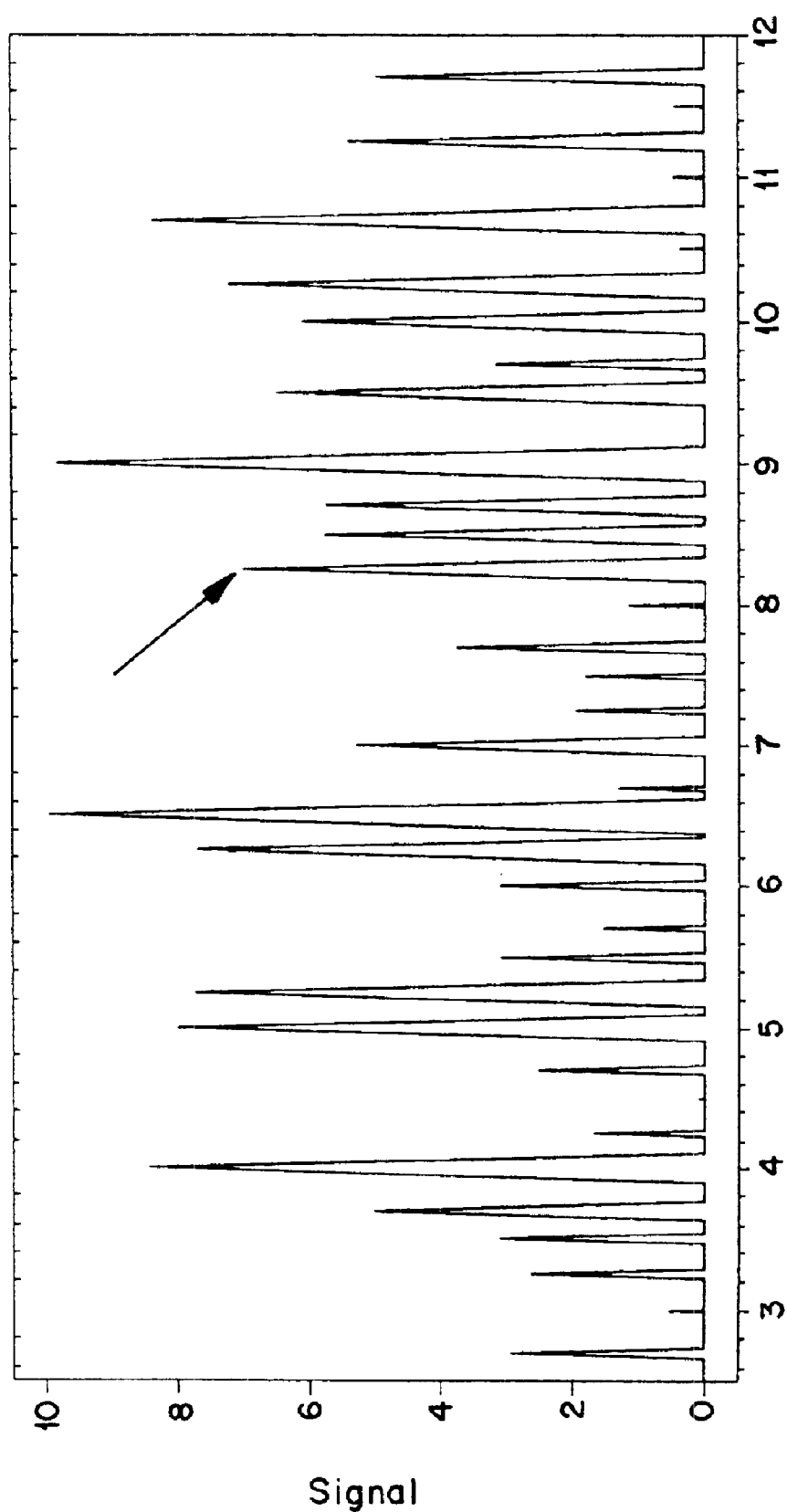
Figure 5C:
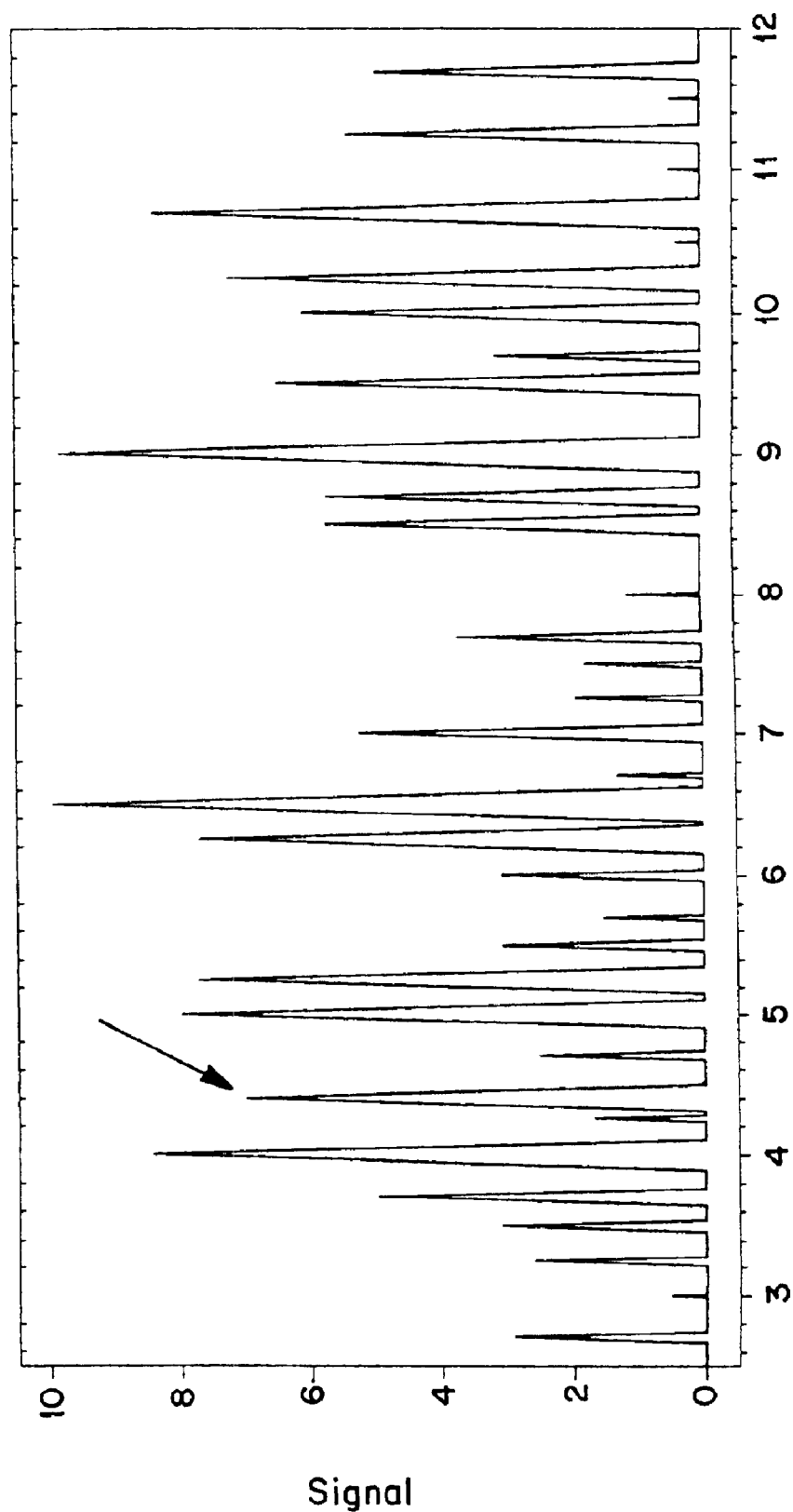
Figure 6B:
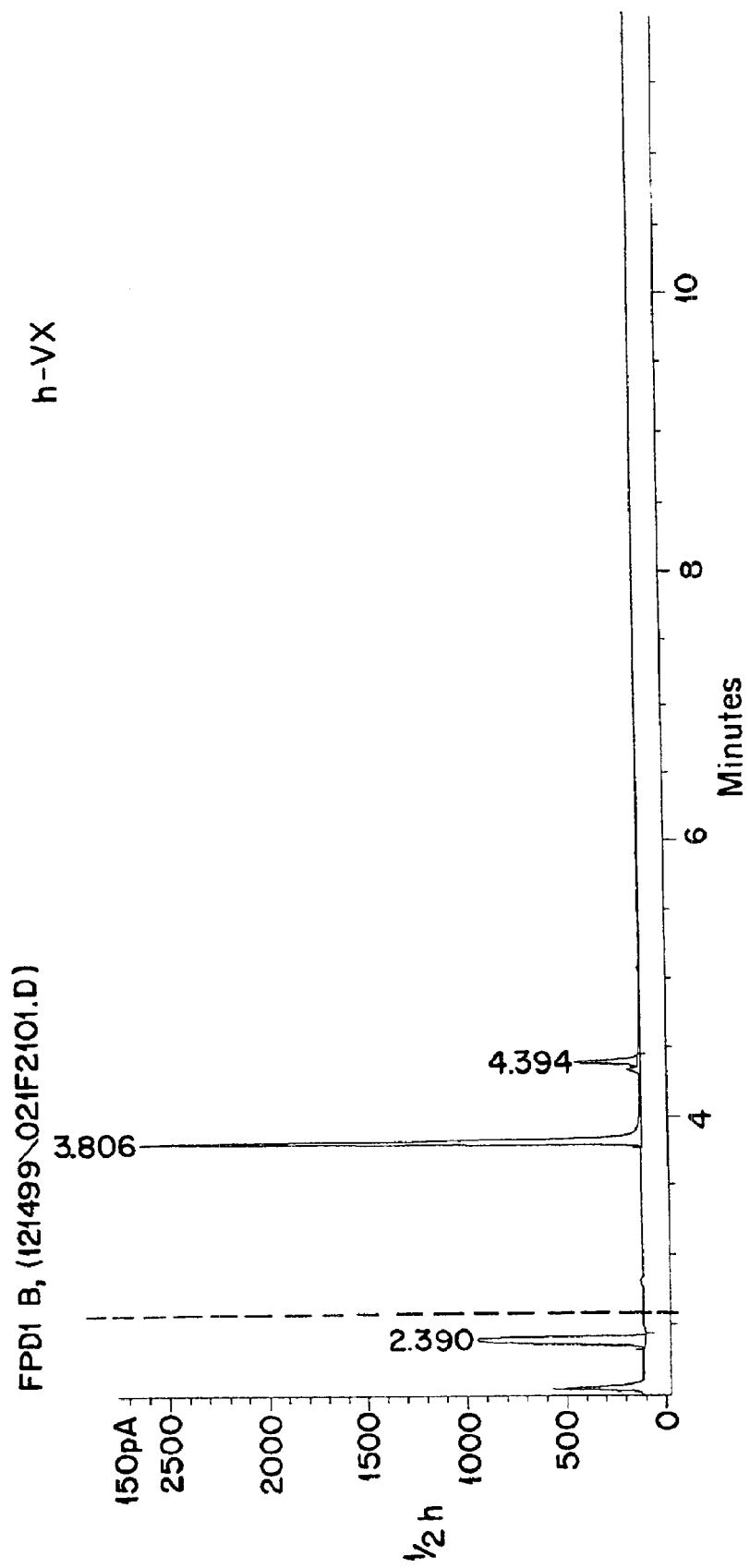
Figure 6C:
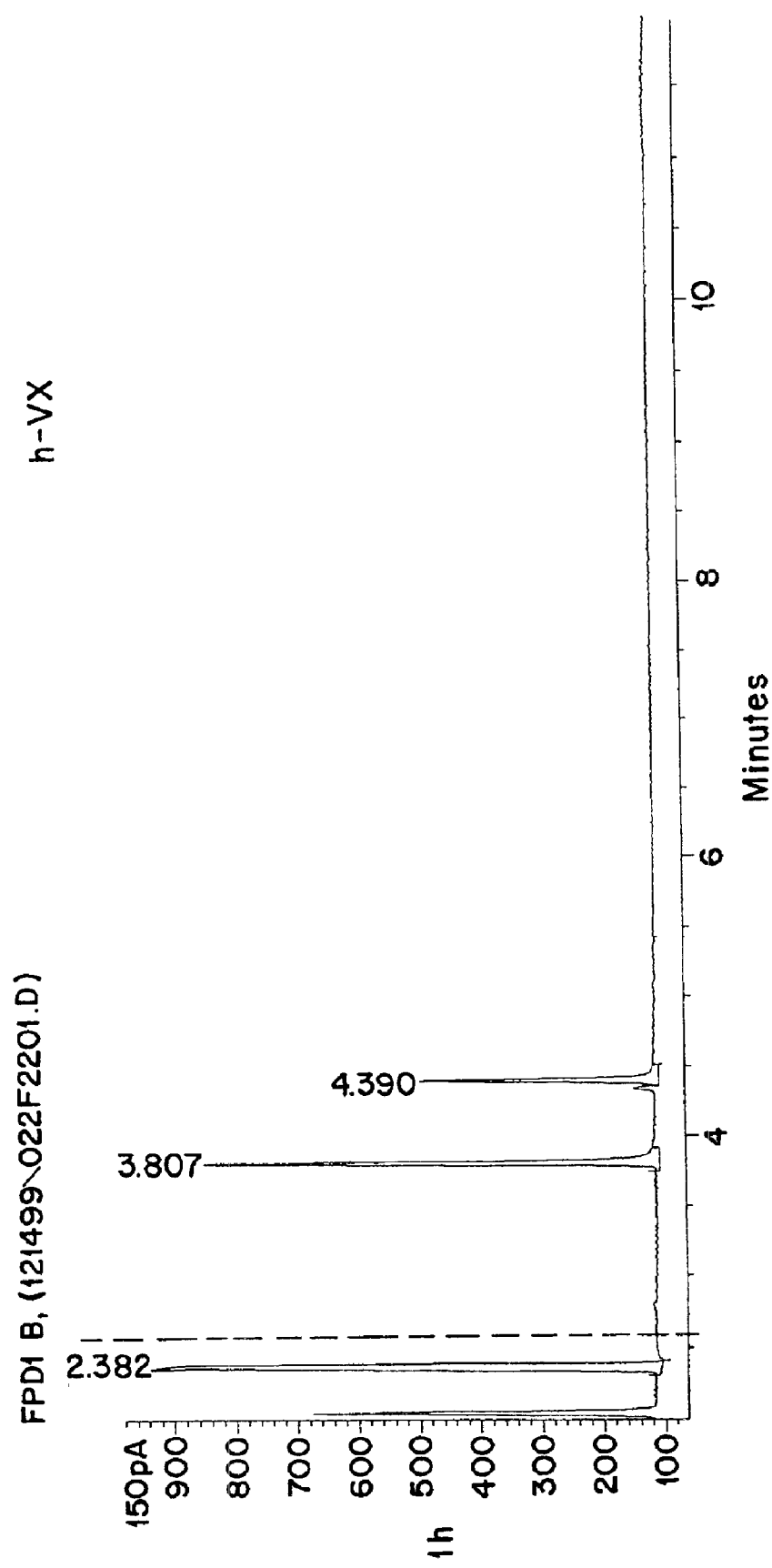
Figure 6D:
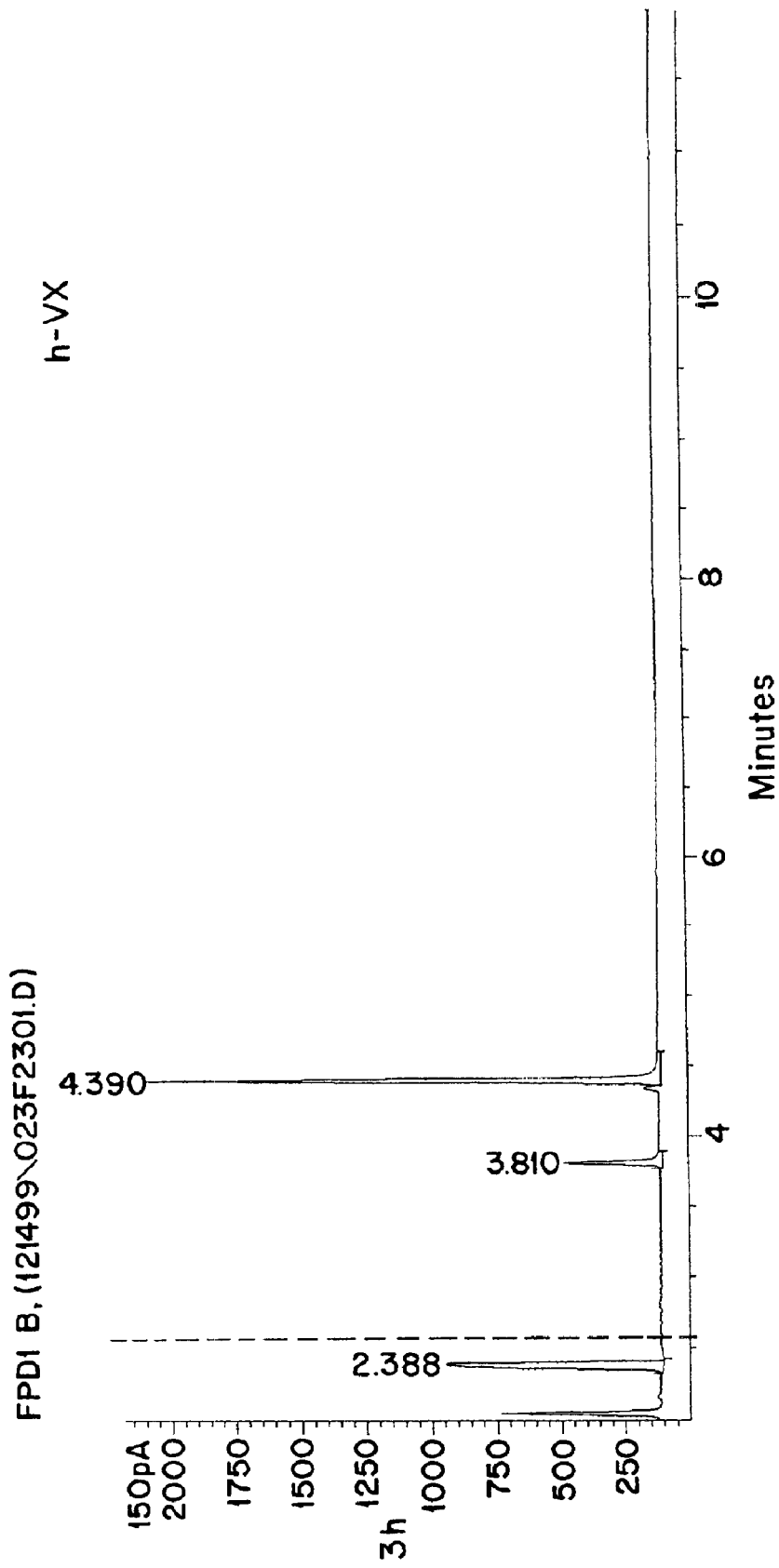
Figure 6E:
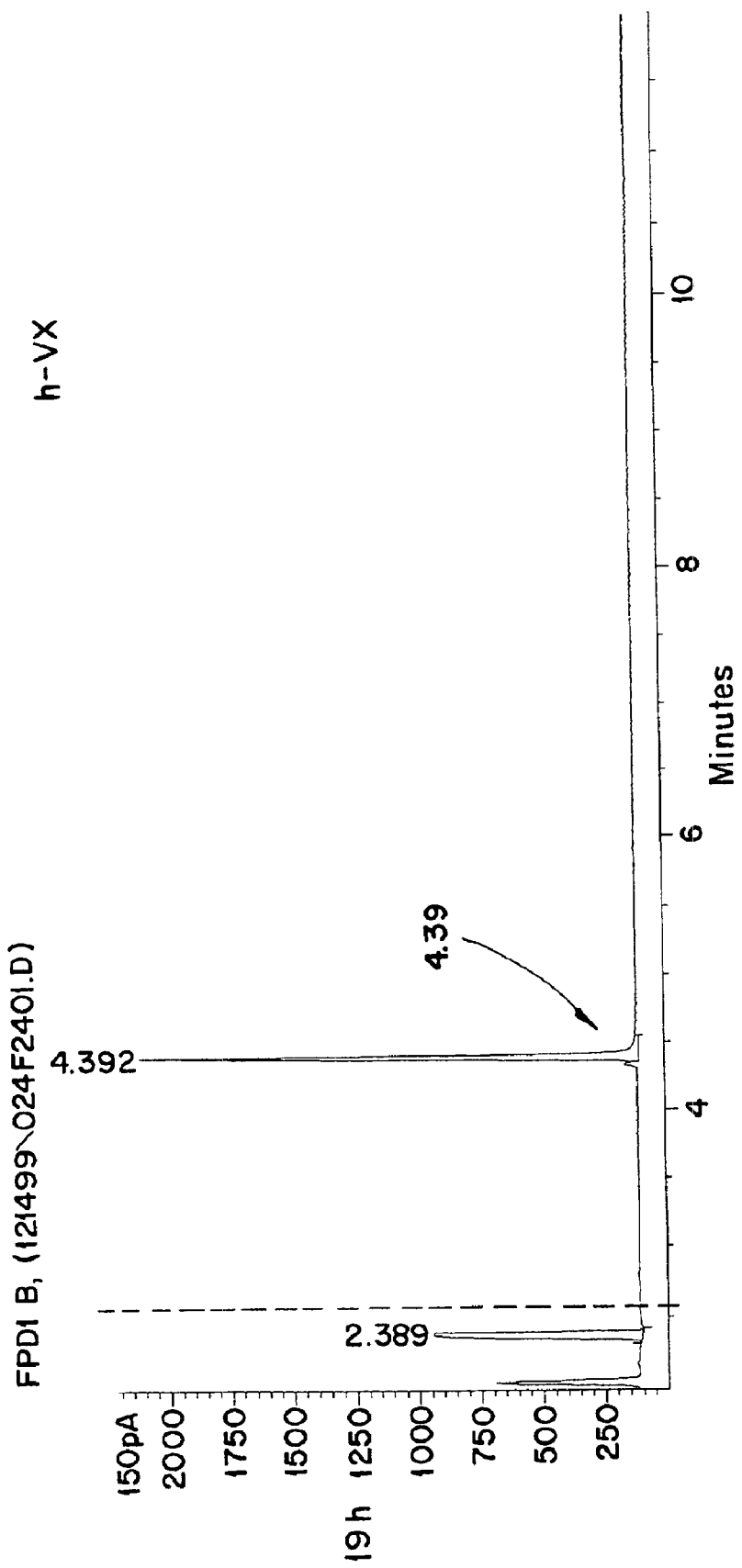
Figure 6F:
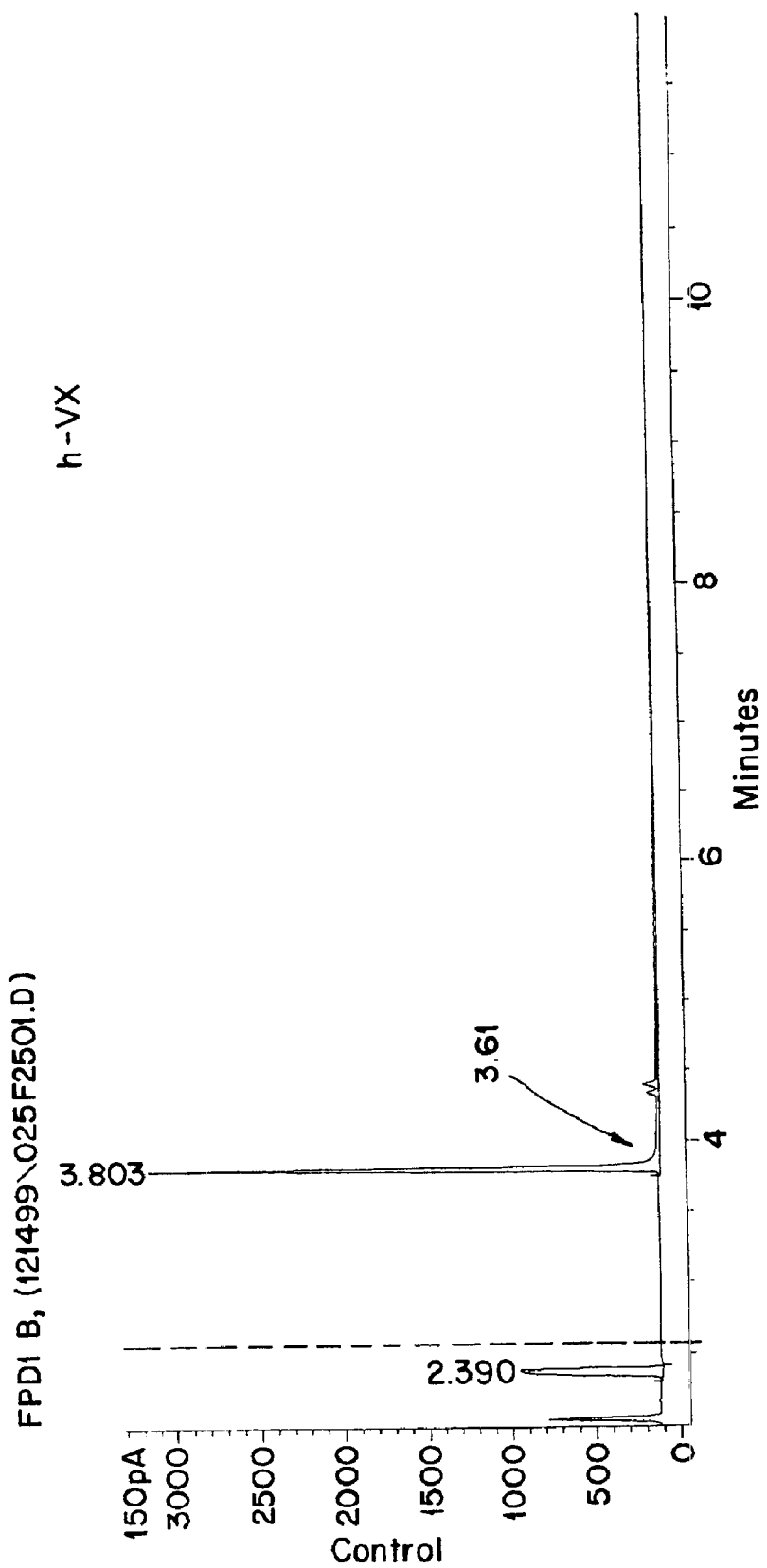
Figure 6G:
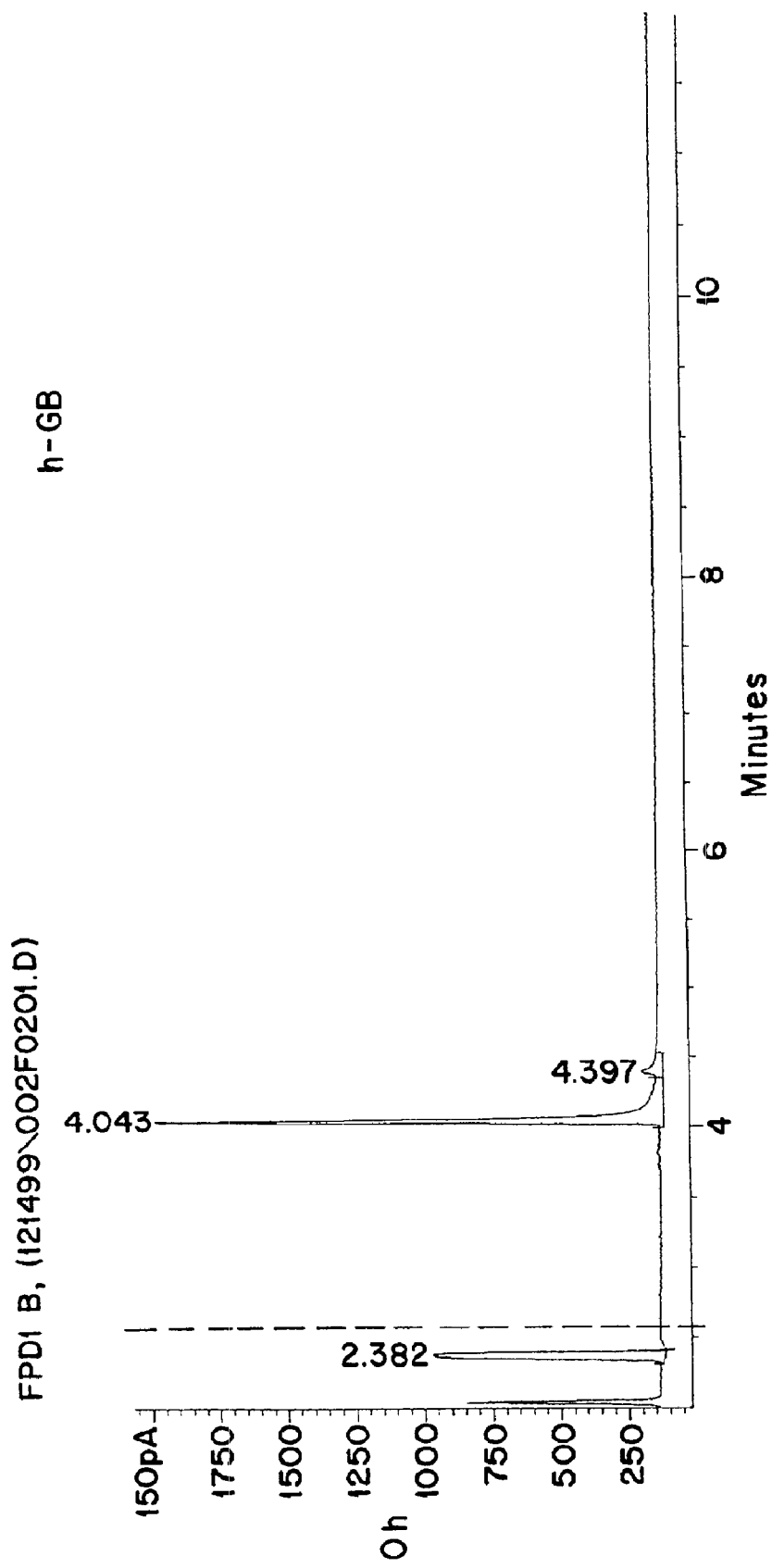
Figure 6H:
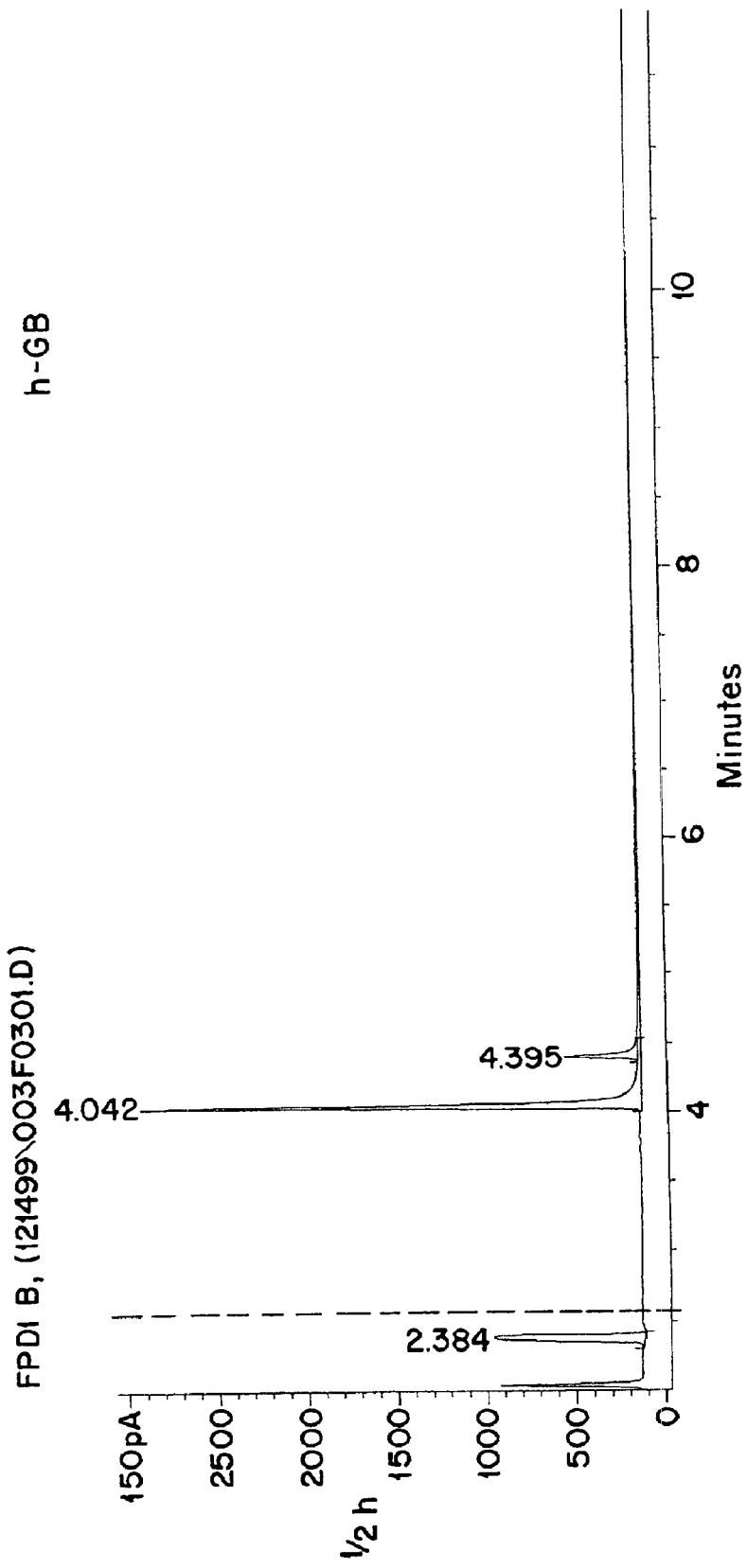
Figure 61:
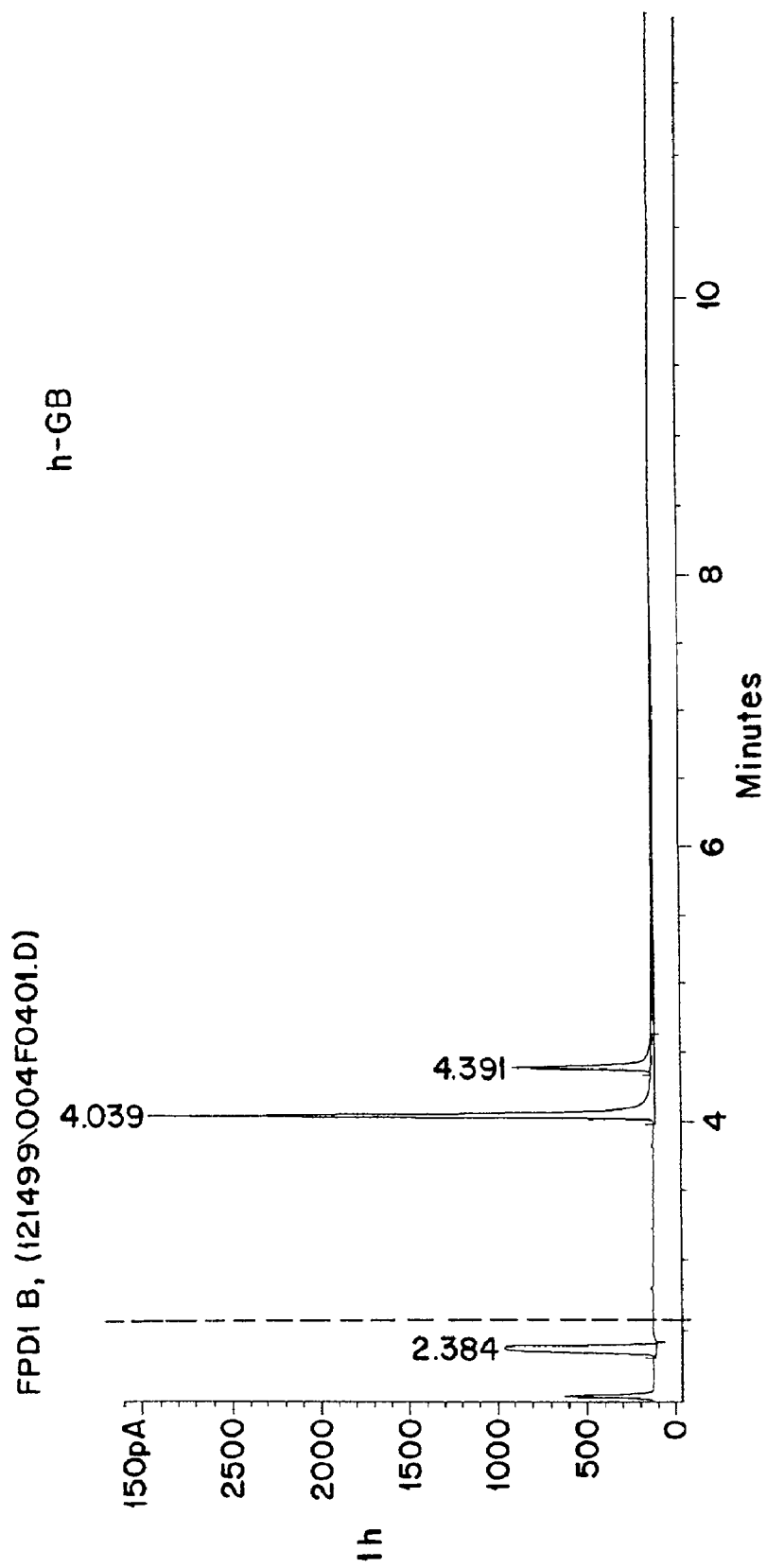
Figure 6J:
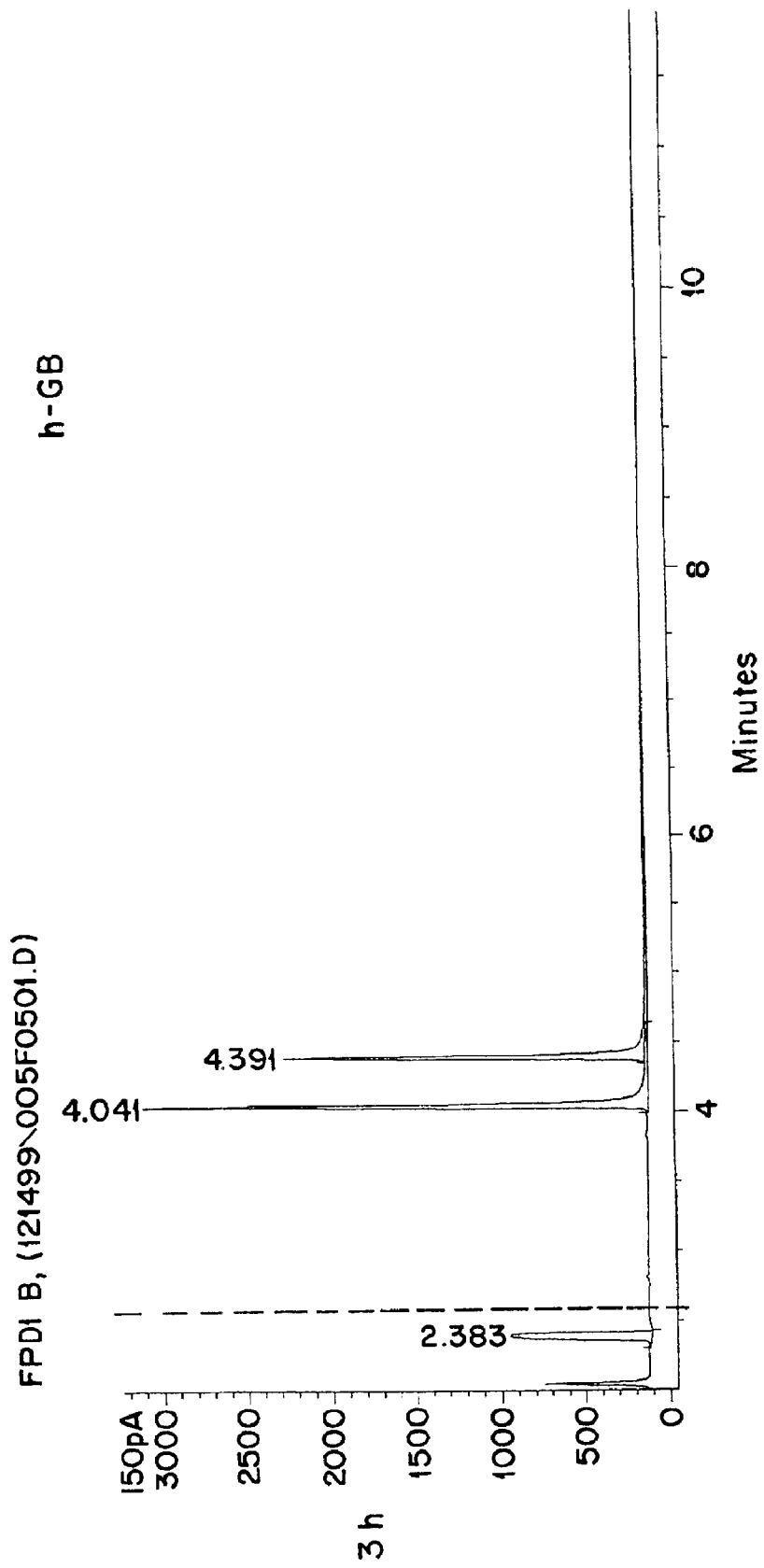
Figure 6L:
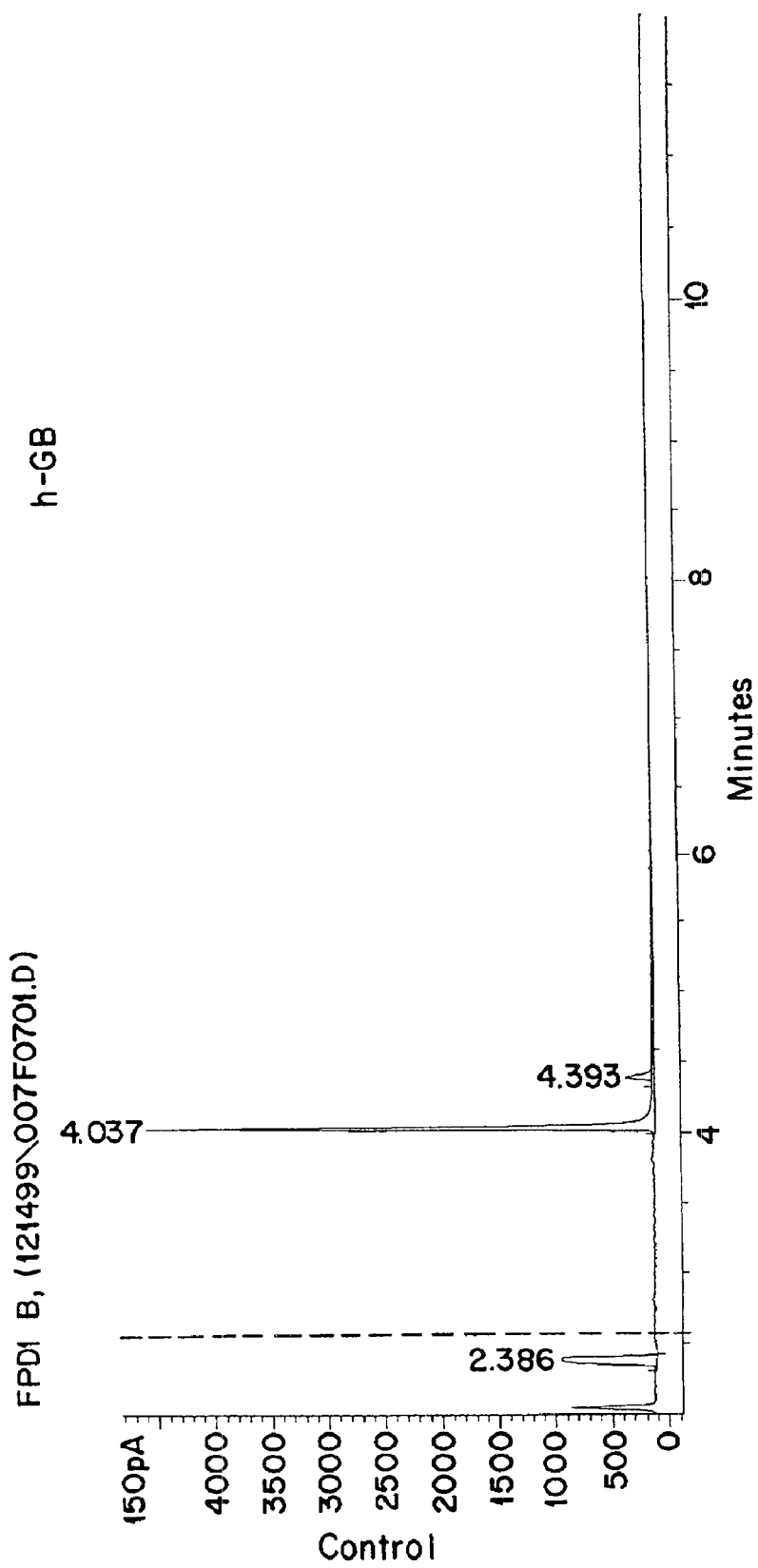
Figure 7D:
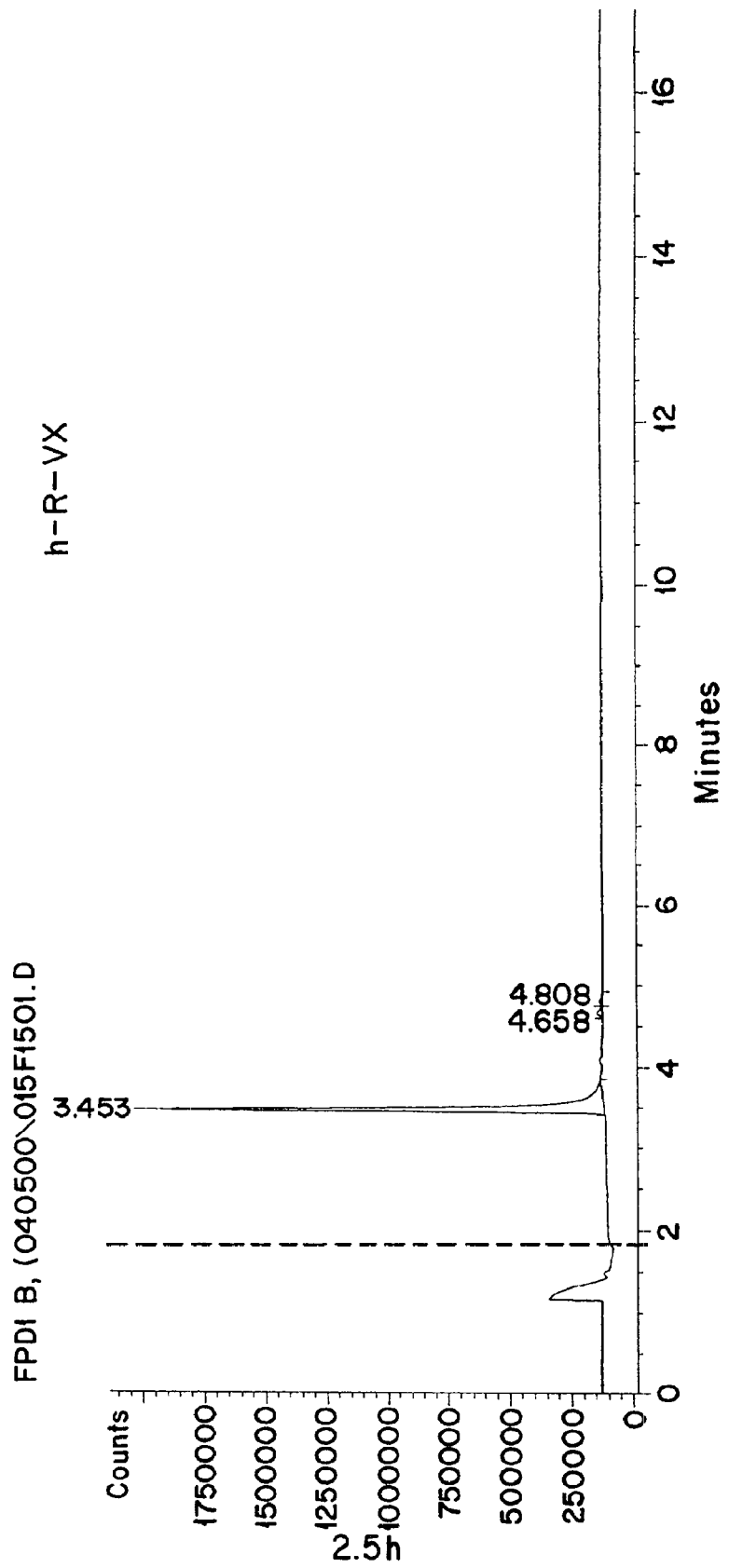
Figure 7E:
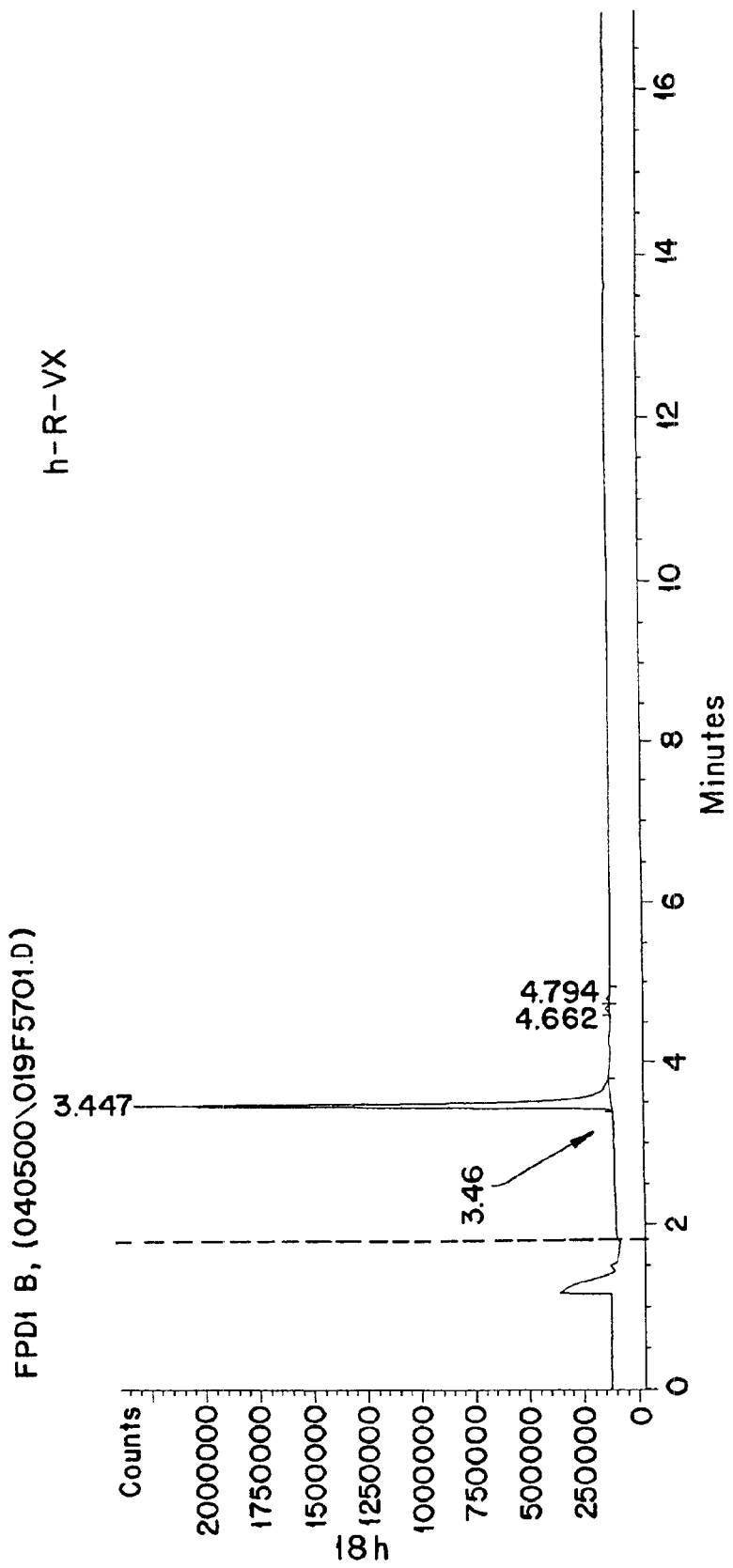

Table 2 gives the anticipated compositions of the sample before (NONE) and after treatment by different combinations of the three enzymes, OPH, OPAA and PEH. The table shows the specific "fingerprints" that would be generated from the CW OP agents based on methylphosphonate esters due to the differences in characteristics among agents, as well as among their respective phosphonate esters (for example see Table 1). Table 1 gives the experimental retention times of the five CW OP agents and their degraded phospho-products on GC-FPD using the standard protocol parameters of our lab. FIG. 5 illustrates the basic approach for utilizing the information from tables 1 and 2 for the identification of GF agent. In this example, the appearance of the ~4.4 min peak corresponding to sililated methylphosphonic acid and the concomitant disappearance of the ~8.2 min peak corresponding to sililated cyclohexyl methylphosphonic acid from OPH/OPAA/PEH treated sample (panel c) that was present in OPH/OPAA treated sample (panel b) would suggest the presence of h-GF in OPH/OPAA treated sample. Similarly, the disappearance of the ~9.2 min peak corresponding to GF in the OPH/OPAA treated sample that was present in the untreated sample (panel a) and the concomitant appearance of the ~8.2 min peak corresponding to sililated cyclohexyl methylphosphonic acid (derivatized) (panel b) would indicate the presence of GF in the untreated sample. This example indicates the desirability of a database (especially for aryl- and alkyl-phosphonic acids, the terminal phospho-products of the degradation pathway) for identification purposes. However, even in the absence of a database, the changes in the retention times from OPH/OPAA-treated to OPH/OPAA/PEH-treated samples could be indicative of the agent's presence and could be used both for screening and for further interrogating these products by GC/MS.

TABLE 2

Expected sample compositions before and after OPH/OPAA and PEH treatments.

| NONE | OPH/OPAA | PEH | OPH/OPAA/PEH |
|---|---|---|---|
| Agent | MPE | Agent | MPn |
| Agent + MPE | MPE | Agent + MPn | MPn |
| MPE + MPn | MPE + MPn | MPn | MPn |
| MPn | MPn | MPn | MPn |
| MPE | MPE | MPn | MPn |
| Agent + MPn | MPE + MPn | Agent + MPn | MPn |
| Agent + MPn + MPE | MPE + MPn | Agent + MPn | MPn |

MPE=methylphosphonate ester MPn=methylphosphonic acid.

Benefits and advantages of our invention include (1) the development of a new analytical capability for unknown CW OP neurotoxins that is based on phosphonate esters, (2) a vast improvement in reliability and speed over the existing analytical methodologies for both known and unknown neurotoxins possessing phosphonate ester moieties, and (3) a new analytical capability for phosphonate ester degradation products for both known and unknown neurotoxins. The methods described herein offer substantial cost savings associated with the analysis of "unknown" samples for an enormous variety of possible G- and V-type agents. Rather than analyze instrumental output for the appearance of agent peaks against noisy backgrounds, the samples may be treated with an enzyme mixture and evaluated for the appearance of the MPn peak, indicative of the presence of CW OP. Positive samples are then evaluated against the enzyme-digest "fingerprint" for agent identification.

It is contemplated that the methods, compositions and kits of this invention would be suitable for many applications, both military and civilian. Significant effort is devoted by the US military to develop sensors for agent detection. Two leading signal-transducing technologies that are considered for the sensors are electrochemical (e.g. ion-selective field effect transistor) and acoustic (surface acoustic waveguide). The PEH enzyme (alone and together with OPH/OPAA) could potentially be used on both of these platforms. The effort could also impact on Domestic Preparedness/Homeland Defense and CWC Verification Programs.

The PEH enzymes may be obtained from *B. caryophilli*, such as strain PG2982. Bacteria cells PG2982 were deposited on Mar. 5, 2002 with the ATCC, P.O. Box 1549, Manassas, VA 20108 under Accession No. PTA-4116. The PEH enzymes may be produced and purified using well-established methods (e.g., gel-filtration, ion-exchange, hydroxyapatite, and hydrophobic interaction chromatographies). Substrate specificities for the purified PEH may be ascertained using techniques known in the art for selected alkyl—alkyl-, alkyl-aryl-, aryl-alkyl-, and aryl—aryl-phosphonate esters and pesticide degradation products. The reaction rate kinetics and the optimal reaction conditions may also be ascertained using techniques known in the art. For routine kinetics, GC-FPD may be used for silylated derivatives of the analytes. The enzymes may be produced, purified, and freeze-dried. GC-FPD/MS may be used for database and agent identification.

Two different assay methods may be used for monitoring PEH activity. For screening large numbers of samples (e.g., chromatographic effluents), chromogenic substrate may be used in calorimetric assays. Samples showing activity for the chromogenic substrate may be evaluated further with selected hydrolyzed-agent substrates using GC-FPD for silylated derivatives of the analytes. GC-FPD analysis may also be used to study the enzymatic hydrolysis of agents. For VX and R-VX degradation studies, in addition to the GC-FPD analysis, Eliman's reagent/DTNB colorimetric method may be used.

Methods for obtaining OPH are described in U.S. Pat. No. 5,589,386, Methods for obtaining OPAA are described in U.S. Pat. No. 5,928,927 and U.S. Pat. No. 6,080,566.

The invention also contemplates an analytical database cataloguing GB, GD, GF, VX and Russian VX selected alkyl- and aryl-phosphonates and alkyl—alkyl-, alkyl-aryl-, aryl-alkyl-, and aryl-arylphosphonate esters and their products. For instance, a modest database consisting of approximately 25–60 compounds may be created without great expense and effort.

REFERENCES

1. Lai K, Stolowich N J, and Wild J R (1995) Characterization of P—S bond hydrolysis in organophosphorothioate pesticides by organophosphorus hydrolase. *Arch. Biochem. Biophys.* 318, 59–64.
2. Dumas D P, Durst H D, Landis W G, Raushel F M, and Wild J R (1990) Inactivation of organophosphorus nerve agents by the phosphotriesterase from *Pseudomonas diminuta*. *Arch. Biochem. Biophys.* 277, 155–159.
3. Rastogi V K, DeFrank J J, Cheng T C, and Wild J R (1997) Enzymatic hydrolysis of Russian-VX by organophosphorus hydrolase. *Biochem. Biophys. Res. Commun.* 241, 294–296.
4. Deas R A, DeFrank J J, and Elashvili I (1990) Purification procedures for OPA Anhydrase-2 from halophile JD6.5. *Proceedings of the 1989 U.S. Army Chemical Research, Development and Engineering Center Scientific Conference on Chemical Defense Research*. CRDEC-SP-025, pp 629–636.
5. DeFrank J J, Cheng T C (1991) Purification and properties of an organophosphorus acid anhydrase from a halophilic bacterial isolate. *J. Bacteriol.* 173:6 1938–1943.
6. Elashvili, I., DeFrank, J. J., and Culotta, V. C. (1999) Purification and Characterization of DFPase from *Alteromonas haloplanktis* ATCC 14393. *Proceedings of the 1998 U.S. Army Edgewood Research, Development and Engineering Center Scientific Conference on Chemical and Biological Defense Research*. ECBC-SP-004, pp 763–771.
7. Cheng T C, Rastogi V K, DeFrank J J, Sawiris G P (1998) G-type nerve agent decontamination by *Alteromonas* prolidase. *Ann. NY Acad. Sci.* 864, 253–258.
8. Cheng T, Liu L, Wang B, Wu J, DeFrank J J, Anderson D M, Rastogi V K, Hamilton A B (1997) Nucleotide sequence of a gene encoding an organophosphorus nerve agent degrading enzyme from *Alteromonas haloplnktis*. *J Ind. Microbiol. Biotechnol.* 18:1, 49–55.
9. Cheng T C, DeFrank J J, and Rastogi V K (1999) *Alteromonas* prolidase for organophosphorus G-agent decontamination *Chem. Biol. Interact.* 119–120, 455–462.
10. Elashvili, I., DeFrank, J. J. (2000) Enzymatic hydrolysis of neutralized nerve agents. *American Society for Microbiology, 100th General Meeting Abstracts*, pg. 436. (abstract)
11. Elashvili, I. and DeFrank, J. J. (2001) Furthering the Enzymatic Destruction of Nerve Agents. *Proceedings of the 2001 Scientific Conference on Chemical and Biological Defense Research* (in press).
12. Nakajima T, Sasaki K, Ozawa H, Sekjima Y, Morita H, Fukushima Y, and Yanagisawa N (1998) Urinary metabolite of sarin in a patient of the Matsumoto sarin incident. *Arch. Toxicol.* 72, 601–603.
13. Shih M L, McMonagle J D, Dolzine T W, and Gresham V C (1994) Metabolite pharmacokinetics of soman, sarin and GF in rats and biological monitoring of exposure to toxic organophosphorus agents. *J Appl Toxicol.* 14, 195–199.

All references cited herein are incorporated by reference in their entirety. All examples described herein are intended for illustrative purposes only, and persons having ordinary skill in this art would understand that the total scope of the invention should not be limited to the specific parameters and results of these examples.

What is claimed:

1. A method for detecting a chemical warfare agent that contains organophosphorus compounds, comprising the steps of:
   (a) contacting a liquid sample suspected of containing chemical warfare agents that contain organophosphorus compounds, degradation products thereof, chemical warfare agent precursors, and mixtures thereof with a sufficient amount of phosphonate ester hydrolase, a sufficient amount of organophosphorus hydrolase, and a sufficient amount of a organophosphorus acid anhydrolase, and
   (b) detecting the presence of phosphonate which presence is indicative of a chemical warfare agent that contains organophosphorus compounds.

2. The method of claim 1, wherein the chemical warfare agent that contains organophosphorus compounds is selected from the group consisting of GB, GC, GF, VX and Russian VX.

3. The method of claim 1, wherein the presence of phosphonate is detected using liquid or gas chromatography.

4. The method of claim 1, wherein the presence of phosphonate is detected using mass spectrometry.

5. The method of claim 1, wherein the presence of phosphonate is detected using both liquid chromatography and mass spectrometry.

6. The method of claim 1, wherein the presence of phosphonate is detected using both gas chromatography and a flame photometric detector and phosphorus filter.

7. The method-of claim 1, wherein the amount of phosphonate ester hydrolase is at least about 0.5 EMPA units.

8. The method of claim 1, wherein the amount of organophosphorus hydrolase is at least about 25 DFP units.

9. The method of claim 1, wherein the amount of organophosphorus acid anhydrolase is at least about 25 DFP units.

10. The method of claim 1, wherein the amount of phosphonate ester hydrolase is at least about 0.5 EMPA units, the amount of organophosphorus hydrolase is at least about 25 DFP units, and the amount of organophosphorus acid anhydrolase is at least about 25 DFP units.

11. The method of claim 1, which comprises the further steps of:
   (c) contacting a portion of the liquid sample with organophosphorus hydrolase and organophosphorus acid anhydrolase;
   (d) contacting another portion of the liquid sample with phosphonate ester hydrolase;
   (e) contacting another portion of the liquid sample with organophosphorus hydrolase, organophosphorus acid anhydrolase, and phosphonate ester hydrolase; and (f) analyzing the respective portions of the liquid samples of step (c), (d) and (e) to determine the components of each portion.

12. The method of claim 1, which comprises the further steps of
   (c) contacting a portion of the liquid sample with an alkaline substance and neutralizing the sample, (d) contacting a portion of the liquid sample of step (c) phosphonate ester hydrolase; (e) contacting another portion of the liquid sample with phosphonate ester hydrolase; and
   (f) analyzing the respective portions of the liquid sample of steps (c), (d) and (e) to determine the components of each portion.

13. The method of claim 11, wherein step (f) is carried out using a gas chromatography device.

14. The method of claim 12, wherein step (f) is carried out using a gas chromatography device.

15. The method of claim 1, wherein the phosphonate is methylphosphonate.

16. A method for detecting a chemical warfare agent that contains organophosphorus compounds, comprising the steps of:
   (a) contacting a liquid sample suspected of containing chemical warfare agents that contain organophosphorus compounds, degradation products thereof, chemical warfare agent precursors, and mixtures thereof with sufficient amount of an alkanine substance, under conditions to convert the chemical warfare agents that contain organophosphorus compounds, degradation products thereof, chemical warfare agent precursors, and mixtures thereof to a corresponding phosphonate ester;
   (b) neutralizing the solution of step (a);
   (c) contacting the solution of step (b) with a sufficient amount of phosphonate ester hydrolase, under conditions to convert the phosphonate ester to its corresponding phosphonate; and
   (d) detecting the presence of phosphonate which presence is indicative of a chemical warfare agent that contains organophosphorus compounds.

17. The method of claim 16, wherein the chemical warfare agent that contains organophosphorus compounds is selected from the group consisting of GB, GC, GF, VX and Russian VX.

18. The method of claim 16, wherein the presence of phosphonate is detected using liquid or gas chromatography.

19. The method of claim 16, wherein the presence of phosphonate is detected using mass spectrometry.

20. The method of claim 16, wherein the presence of phosphonate is detected using both liquid chromatography and mass spectrometry.

21. The method of claim 16, wherein the presence of phosphonate is detected using both gas chromatography and a flame photometric detector and phosphorus filter.

22. The method of claim 16, wherein the amount of phosphonate ester hydrolase is at least about 0.5 EMPA units.

23. The method of claim 16 wherein the phosphonate is methylphosphonate.

24. A composition capable of degrading chemical warfare agents that contains organophosphorus compounds, precursors of organophosphorus compounds, and/or their degradation products, which composition comprises phosphonate ester hydrolase, organophosphorus hydrolase, and organophosphorus acid anhydrolase.

25. The composition of claim 24, which comprises at least about 0.5 EMPA units phosphonate ester hydrolase, at least about 25 DFP units organophosphorus hydrolase, and at least about 25 DFP units organophosphorus acid anhydrolase.

26. A kit for detecting the presence of chemical warfare agents that contain organophosphorus compounds, degradation products thereof, or precursors of organophosphorus compounds, comprising, packaged in association:
   (a) phosphonate ester hydrolase,
   (b) organophosphorus hydrolase,
   (c) organophosphorus acid anhydrolase, and
   (d) a detection device for detecting the presence of phosphonate which presence is indicative of chemical warfare agents that contain organophosphorus compounds.

27. A kit for detecting the presence of chemical warfare agents that contain organophosphorus compounds, degradation products thereof, or precursors of organophosphorus compounds, comprising, packaged in association:
   (a) phosphonate ester hydrolase,
   (b) an alkaline compound,
   (c) a neutralization agent, and
   (d) a detection device for detecting the presence of phosphonate which presence is indicative of chemical warfare agents that contain organophosphorus compounds.

* * * * *